(12) United States Patent
Alheidt et al.

(10) Patent No.: US 8,062,252 B2
(45) Date of Patent: Nov. 22, 2011

(54) SAFETY SHIELD SYSTEM FOR A SYRINGE

(75) Inventors: Tom Alheidt, Lake Stockholm, NJ (US);
Vu Phan, Piscataway, NJ (US); Laurent Barrelle, Saint Nizier du Moucherotte (FR); Bruno Baney, Claix (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 93 days.

(21) Appl. No.: 11/061,912

(22) Filed: Feb. 18, 2005

(65) Prior Publication Data
US 2006/0189933 A1 Aug. 24, 2006

(51) Int. Cl.
*A61M 5/00* (2006.01)
*A61M 5/32* (2006.01)

(52) U.S. Cl. .................. 604/110; 128/919; 604/198
(58) Field of Classification Search .......... 604/110, 604/192–198
See application file for complete search history.

(56) References Cited

U.S. PATENT DOCUMENTS

| | | | |
|---|---|---|---|
| 4,573,976 A | 3/1986 | Sampson | |
| 4,631,057 A | 12/1986 | Mitchell | |
| 4,737,144 A * | 4/1988 | Choksi | 604/198 |
| 4,747,831 A | 5/1988 | Kulli | |
| 4,795,432 A | 1/1989 | Karczmer | |
| 4,813,940 A | 3/1989 | Parry | |
| 4,923,447 A * | 5/1990 | Morgan | 604/198 |
| 4,985,021 A | 1/1991 | Straw | |
| 4,994,045 A * | 2/1991 | Ranford | 604/198 |
| 4,998,920 A | 3/1991 | Johnson | |
| 5,026,356 A | 6/1991 | Smith | |
| 5,053,018 A | 10/1991 | Talonn | |
| 5,061,251 A | 10/1991 | Juhasz | |
| 5,151,088 A | 9/1992 | Allison | |
| 5,156,599 A | 10/1992 | Ranford | |
| 5,163,918 A | 11/1992 | Righi | |
| 5,193,552 A | 3/1993 | Columbus | |
| 5,197,953 A | 3/1993 | Colonna | |
| 5,201,708 A | 4/1993 | Martin | |
| 5,217,437 A | 6/1993 | Talonn | |
| 5,242,420 A | 9/1993 | Martin | |
| 5,246,427 A | 9/1993 | Sturman | |
| 5,300,040 A | 4/1994 | Martin | |

(Continued)

FOREIGN PATENT DOCUMENTS
EP 0 307 367 A1 6/1992
(Continued)

*Primary Examiner* — Kevin C Sirmons
*Assistant Examiner* — Michael J Anderson
(74) *Attorney, Agent, or Firm* — David M. Fortunato; Cohen Pontani Lieberman and Pavane LLP

(57) ABSTRACT

A medical device includes a syringe assembly and a shield system for delivering medicament to a patient. The syringe assembly includes a barrel defining a medicament reservoir, and a needle cannula coupled to the barrel and in fluid communication with the reservoir. The shield system has a hub coupled to the syringe barrel, a shield movably arranged on the hub, the shield being movable from a first position disposed from the needle cannula tip to a second position during insertion of the needle into a patient and movable from the second position to a third position covering the needle cannula tip after the needle cannula is removed from the patient. An urging member urges the shield to the third position upon removal of the needle cannula from the patient. A cover sleeve connected to the needle barrel surrounds the hub and the urging member.

43 Claims, 21 Drawing Sheets

U.S. PATENT DOCUMENTS

| | | | |
|---|---|---|---|
| 5,304,149 A | 4/1994 | Morigi | |
| 5,308,332 A | 5/1994 | Dillard, III | |
| 5,312,347 A * | 5/1994 | Osborne et al. | 604/110 |
| 5,312,372 A | 5/1994 | DeHarde et al. | |
| 5,336,176 A | 8/1994 | Yoon | |
| 5,342,309 A | 8/1994 | Hausser | |
| 5,342,320 A | 8/1994 | Cameron | |
| 5,370,628 A | 12/1994 | Allison | |
| 5,385,555 A | 1/1995 | Hausser | |
| 5,389,085 A * | 2/1995 | D'Alessio et al. | 604/198 |
| 5,411,487 A * | 5/1995 | Castagna | 604/198 |
| 5,417,660 A | 5/1995 | Martin | |
| 5,472,430 A * | 12/1995 | Vaillancourt et al. | 604/198 |
| 5,562,626 A | 10/1996 | Sanpietro | |
| 5,591,138 A * | 1/1997 | Vaillancourt | 604/263 |
| 5,651,774 A | 7/1997 | Taranto | |
| 5,658,254 A | 8/1997 | Reichenbach | |
| 5,681,292 A | 10/1997 | Tober | |
| 5,685,862 A * | 11/1997 | Mahurkar | 604/194 |
| 5,713,871 A | 2/1998 | Stock | |
| 5,735,823 A * | 4/1998 | Berger | 604/192 |
| 5,769,822 A | 6/1998 | McGary | |
| 5,795,336 A * | 8/1998 | Romano et al. | 604/192 |
| 5,800,395 A | 9/1998 | Botich | |
| 5,800,403 A | 9/1998 | Pressly | |
| 5,882,342 A | 3/1999 | Cooper | |
| 5,921,959 A * | 7/1999 | McGary et al. | 604/110 |
| 5,984,899 A * | 11/1999 | D'Alessio et al. | 604/198 |
| 6,017,329 A | 1/2000 | Hake | |
| 6,077,253 A | 6/2000 | Cosme | |
| 6,149,629 A * | 11/2000 | Wilson et al. | 604/198 |
| 6,162,197 A * | 12/2000 | Mohammad | 604/195 |
| 6,228,054 B1 | 5/2001 | Dysarz | |
| 6,319,233 B1 * | 11/2001 | Jansen et al. | 604/192 |
| 6,368,303 B1 * | 4/2002 | Caizza | 604/110 |
| 6,379,337 B1 * | 4/2002 | Mohammad M. B. B. S. | 604/195 |
| 6,432,087 B1 | 8/2002 | Hoeck et al. | |
| 6,432,088 B1 | 8/2002 | Huang et al. | |
| 6,440,104 B1 | 8/2002 | Newby et al. | |
| 6,443,929 B1 | 9/2002 | Kuracina | |
| 6,458,101 B1 | 10/2002 | Hu | |
| 6,458,105 B1 | 10/2002 | Rippstein et al. | |
| 6,461,333 B1 | 10/2002 | Frezza | |
| 6,461,362 B1 | 10/2002 | Halseth | |
| 6,475,194 B2 | 11/2002 | Domici, Jr. | |
| 6,478,780 B1 | 11/2002 | Shields | |
| 6,485,469 B1 * | 11/2002 | Stewart et al. | 604/198 |
| 6,494,863 B1 | 12/2002 | Shaw | |
| 6,511,460 B1 | 1/2003 | Arnissolle | |
| 6,514,229 B1 | 2/2003 | Huang | |
| 6,527,742 B1 * | 3/2003 | Malenchek | 604/110 |
| 6,530,903 B2 | 3/2003 | Wang | |
| 6,547,762 B1 | 4/2003 | Botich | |
| 6,558,357 B1 | 5/2003 | Hoeck | |
| 6,565,540 B1 | 5/2003 | Perouse | |
| 6,569,115 B1 | 5/2003 | Barker | |
| 6,569,124 B1 | 5/2003 | Perouse | |
| 6,589,209 B1 | 7/2003 | Dysarz | |
| 6,595,954 B1 | 7/2003 | Luther | |
| 6,605,073 B1 | 8/2003 | Pressly | |
| 6,616,639 B2 * | 9/2003 | Gagnieux et al. | 604/192 |
| 6,626,864 B2 * | 9/2003 | Jansen et al. | 604/110 |
| 6,638,256 B2 * | 10/2003 | Jansen et al. | 604/110 |
| 2002/0026146 A1 * | 2/2002 | Jansen et al. | 604/110 |
| 2002/0065488 A1 | 5/2002 | Suzuki et al. | |
| 2002/0156426 A1 * | 10/2002 | Gagnieux et al. | 604/197 |
| 2002/0193737 A1 | 12/2002 | Popovsky | |
| 2002/0193746 A1 | 12/2002 | Chevallier | |
| 2002/0193747 A1 | 12/2002 | Denolly | |
| 2003/0023205 A1 | 1/2003 | Botich | |
| 2003/0028171 A1 | 2/2003 | DeHarde | |
| 2003/0036730 A1 | 2/2003 | Teichert | |
| 2003/0050601 A1 | 3/2003 | Righi | |
| 2003/0050607 A1 * | 3/2003 | Gagnieux et al. | 604/198 |
| 2003/0078546 A1 | 4/2003 | Jensen | |
| 2003/0083627 A1 | 5/2003 | Chen | |
| 2003/0105430 A1 * | 6/2003 | Lavi et al. | 604/136 |
| 2003/0114799 A1 | 6/2003 | Cheikh | |
| 2003/0144630 A1 * | 7/2003 | Chang et al. | 604/198 |
| 2003/0144631 A1 * | 7/2003 | Doyle et al. | 604/198 |
| 2003/0149403 A1 | 8/2003 | Barker | |
| 2003/0149404 A1 | 8/2003 | Lehmann | |
| 2003/0212380 A1 * | 11/2003 | Barrelle | 604/506 |
| 2005/0027255 A1 * | 2/2005 | Lavi et al. | 604/135 |
| 2006/0189933 A1 * | 8/2006 | Alheidt et al. | 604/110 |

FOREIGN PATENT DOCUMENTS

| | | |
|---|---|---|
| EP | 0 680 767 A1 | 11/1995 |
| EP | 0 864 335 A2 | 9/1996 |
| EP | 0 740 942 A1 | 11/1996 |
| EP | 0 966 983 A1 | 12/1999 |
| EP | 1 258 263 A1 | 11/2002 |
| EP | 1 260 242 A1 | 11/2002 |
| EP | 0 901 391 B1 | 1/2003 |
| EP | 0 963 213 B1 | 1/2003 |
| EP | 1 273 316 A1 | 1/2003 |
| EP | 1 281 410 A1 | 2/2003 |
| EP | 0 916 354 B1 | 3/2003 |
| EP | 1 287 842 A1 | 3/2003 |
| EP | 1 291 029 A1 | 3/2003 |
| EP | 1 291 030 A1 | 3/2003 |
| EP | 1 317 938 A1 | 6/2003 |
| EP | 0 984 804 B1 | 7/2003 |
| EP | 1 329 234 A2 | 7/2003 |
| EP | 0 941 134 B1 | 8/2003 |
| EP | 1 205 173 A2 | 9/2003 |
| EP | 1 205 173 A3 | 9/2003 |
| EP | 0 734 738 B1 | 10/2003 |
| EP | 1 049 503 B1 | 10/2003 |
| FR | 2 830 764 A1 | 4/2003 |
| FR | 2 830 765 A1 | 4/2003 |
| GB | 2 282 069 A | 3/1995 |
| JP | 2001193714 | 12/2002 |
| WO | WO 01/41841 A2 | 6/2001 |
| WO | WO 01/41841 A3 | 6/2001 |
| WO | WO 01/60435 A1 | 8/2001 |
| WO | W0 01/85238 A2 | 11/2001 |
| WO | WO 02/089878 A1 | 11/2002 |
| WO | WO 02/098480 A2 | 12/2002 |
| WO | WO 02/098494 A2 | 12/2002 |
| WO | WO 02/098494 A3 | 12/2002 |
| WO | WO 03/000322 A1 | 1/2003 |
| WO | WO 03/000323 A1 | 1/2003 |
| WO | WO 03/011378 A1 | 2/2003 |
| WO | WO 03/015852 A1 | 2/2003 |
| WO | WO 03/022335 A2 | 3/2003 |
| WO | WO 03/033059 A1 | 4/2003 |
| WO | WO 03/033060 A1 | 4/2003 |
| WO | WO 03/041766 A2 | 5/2003 |
| WO | WO 03/045476 A1 | 6/2003 |
| WO | WO 03/045480 A1 | 6/2003 |
| WO | WO 03/045481 A1 | 6/2003 |
| WO | WO 03/063934 A1 | 8/2003 |
| WO | WO 03/068297 A1 | 8/2003 |
| WO | WO 03/068298 A1 | 8/2003 |

\* cited by examiner

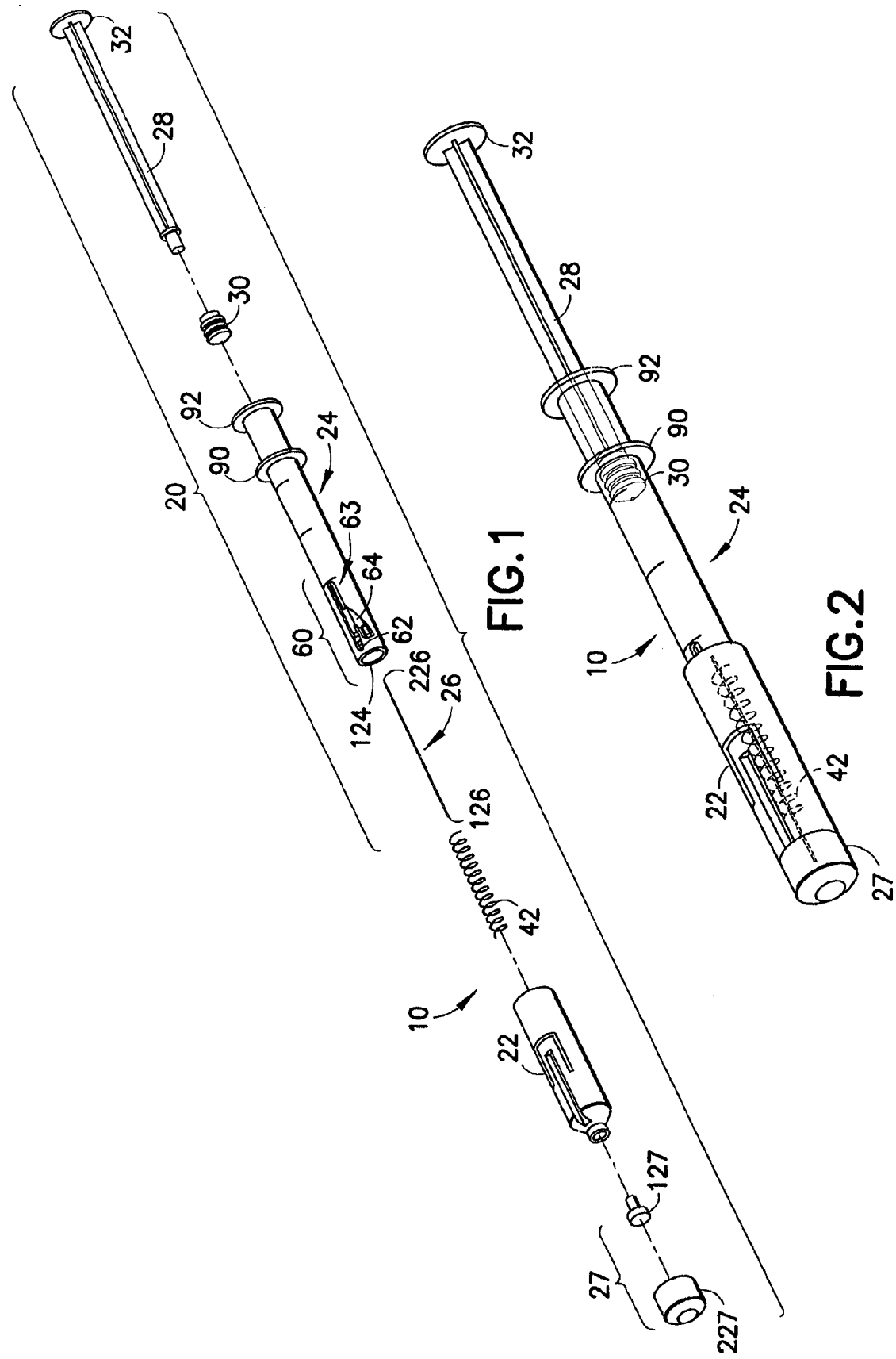

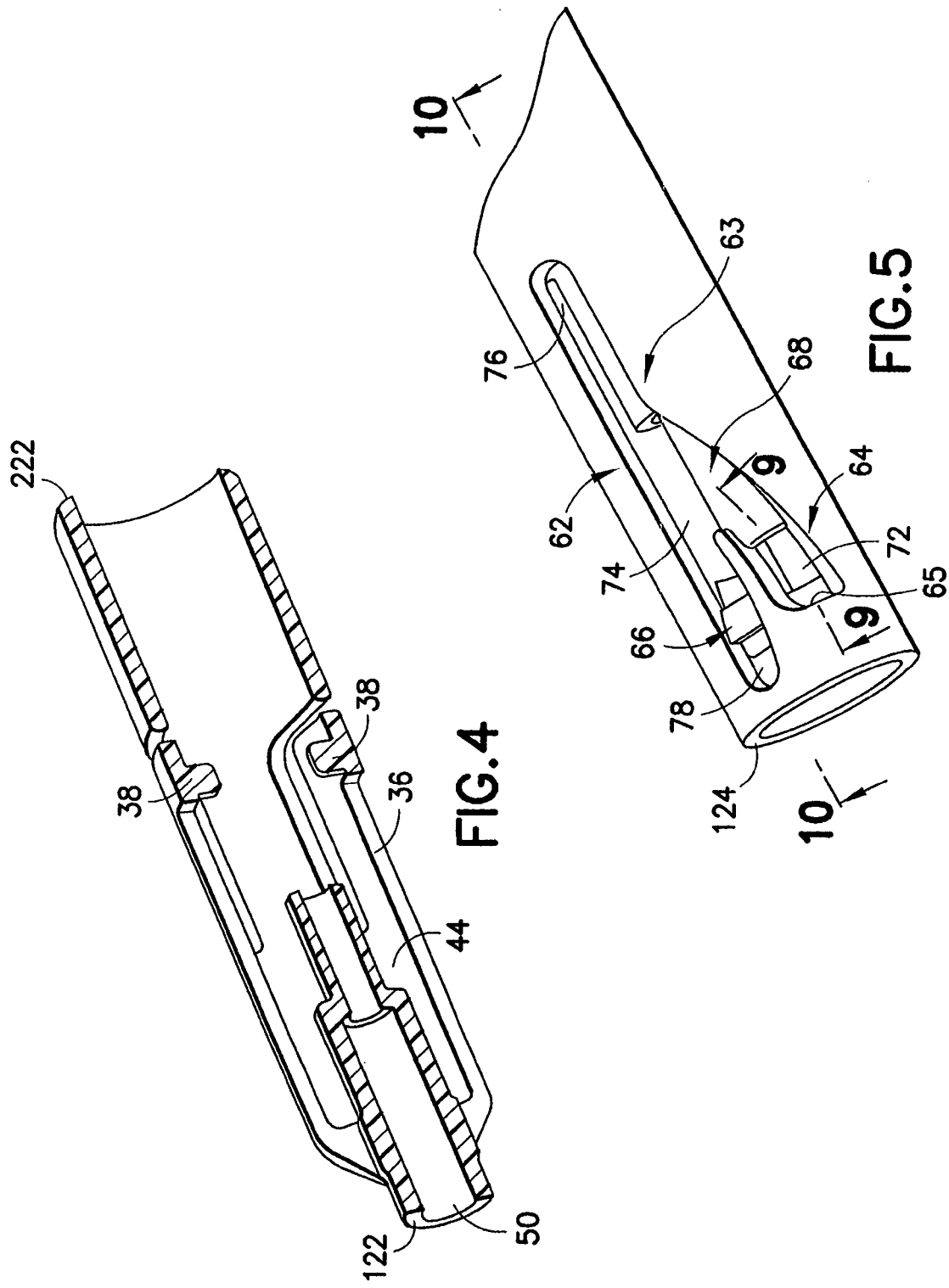

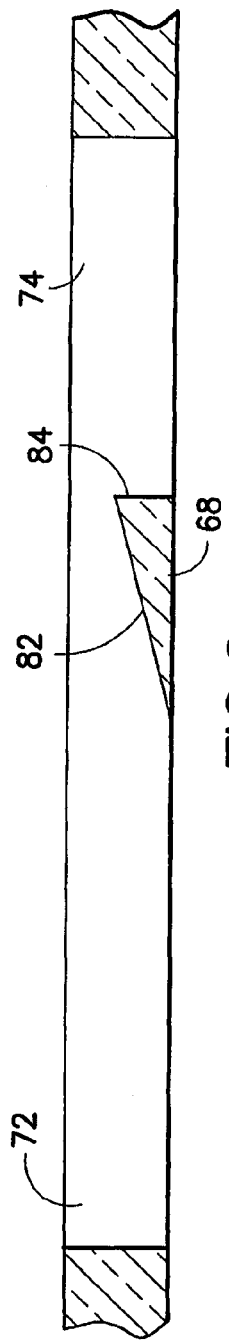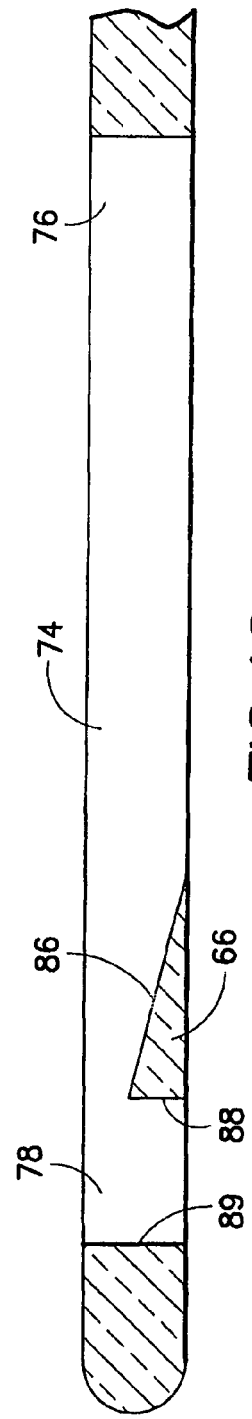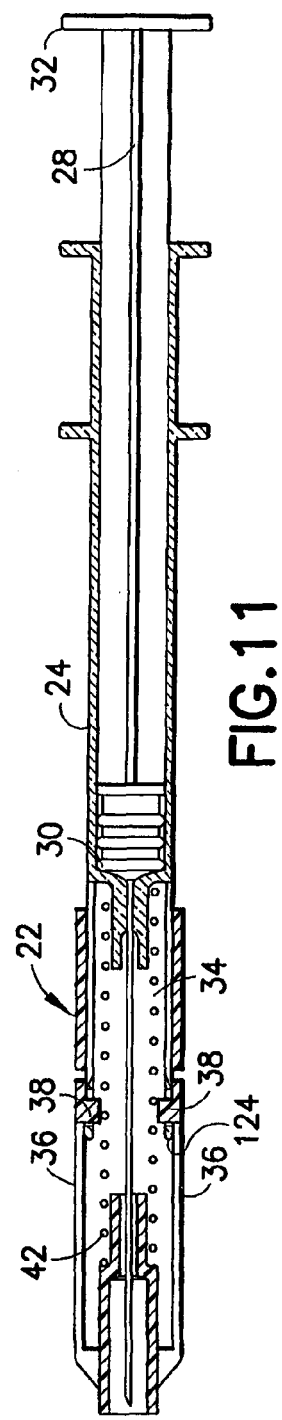

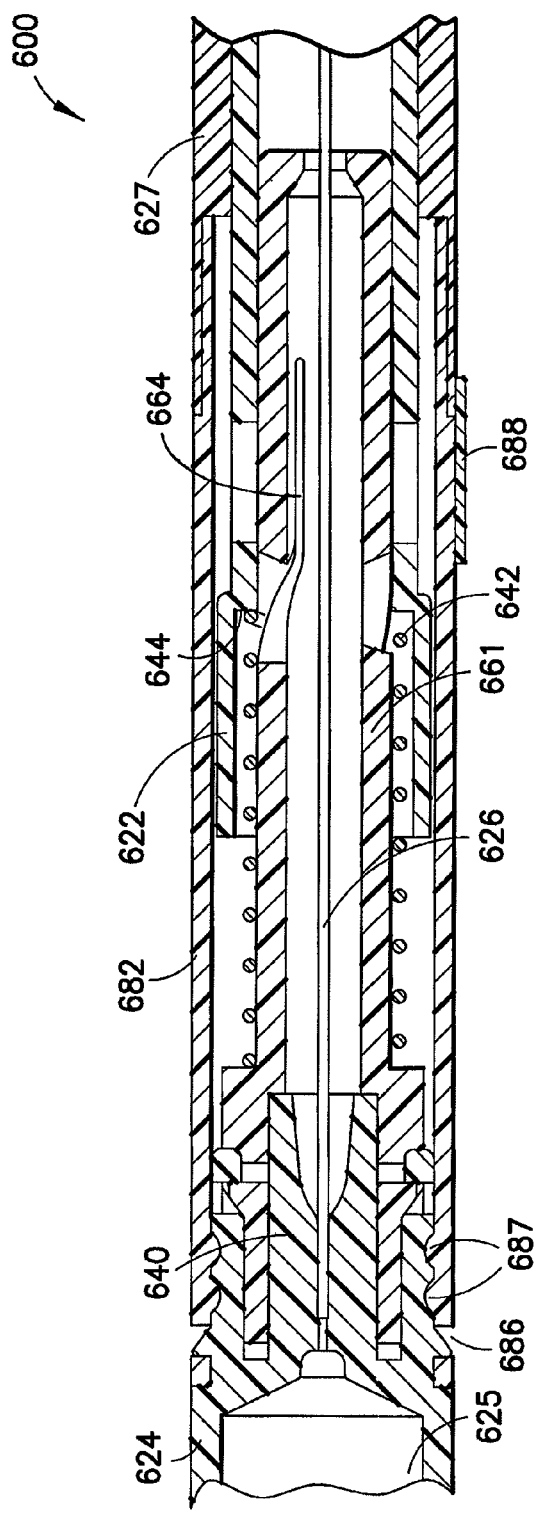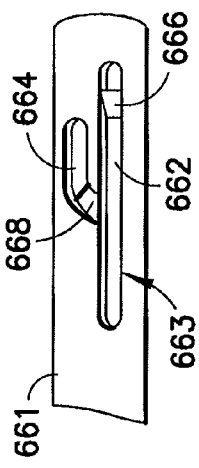

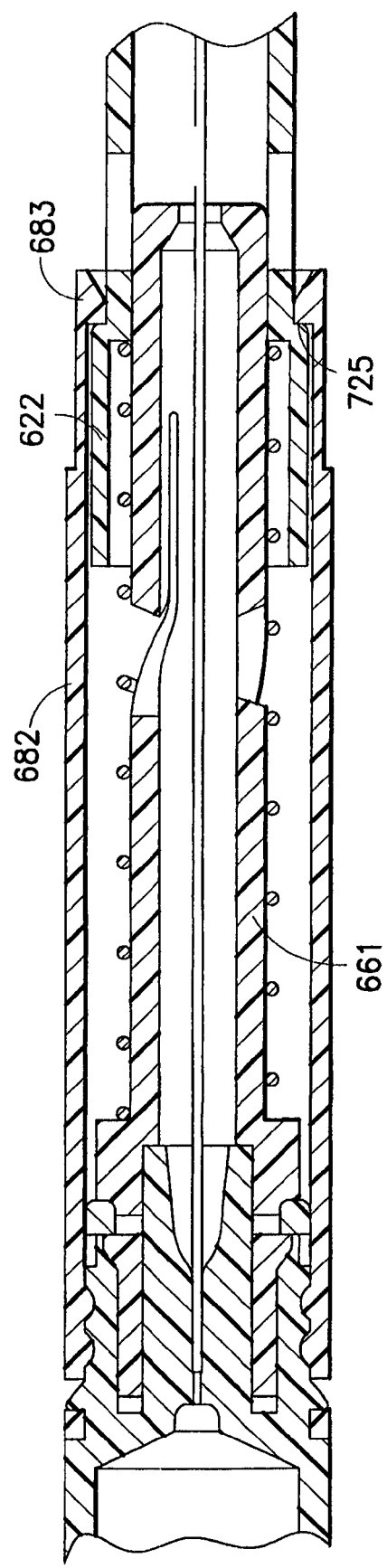

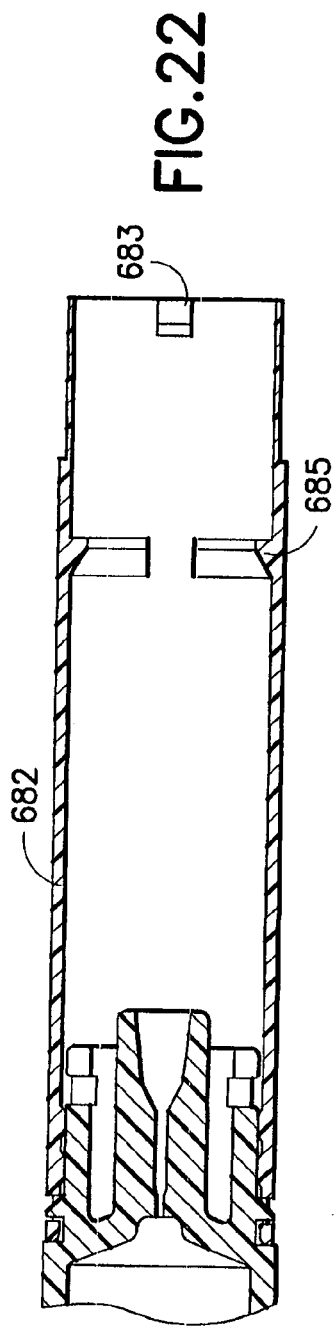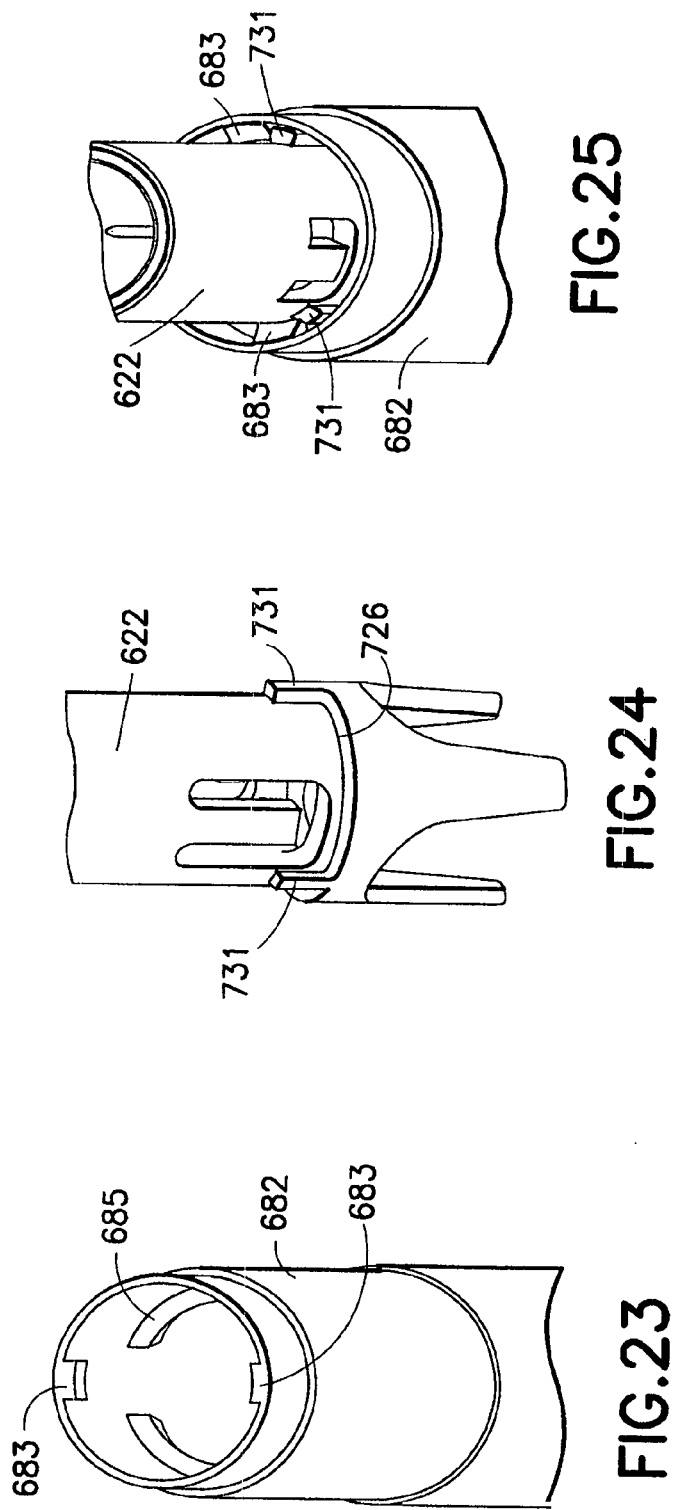

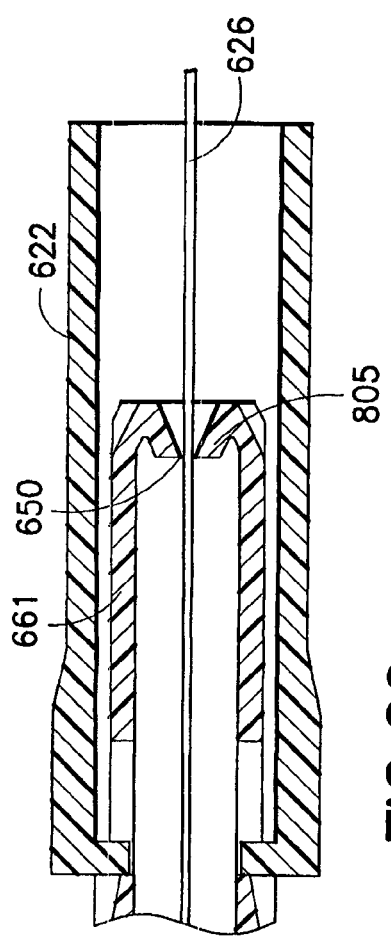
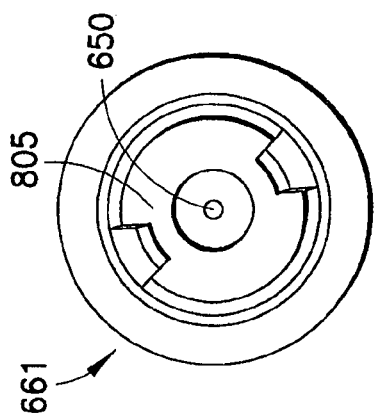
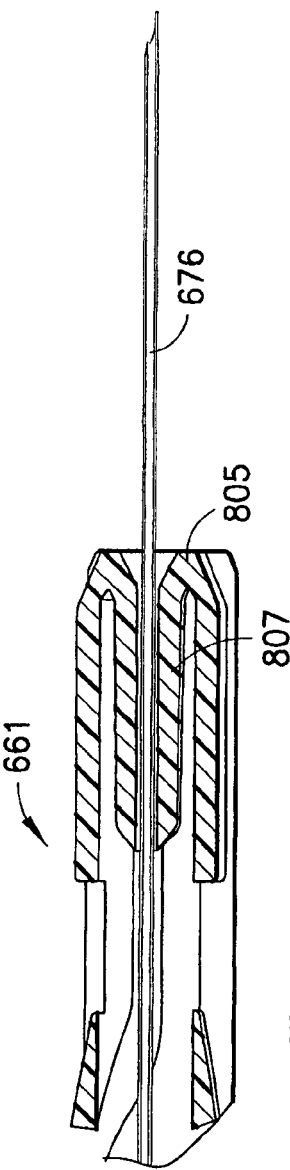
FIG.29
FIG.30
FIG.31

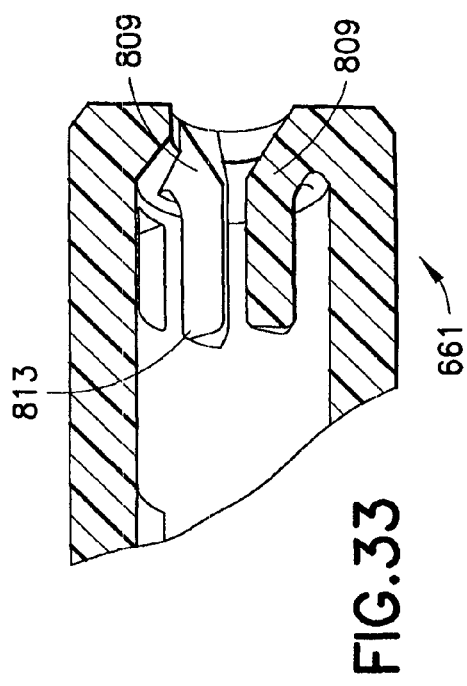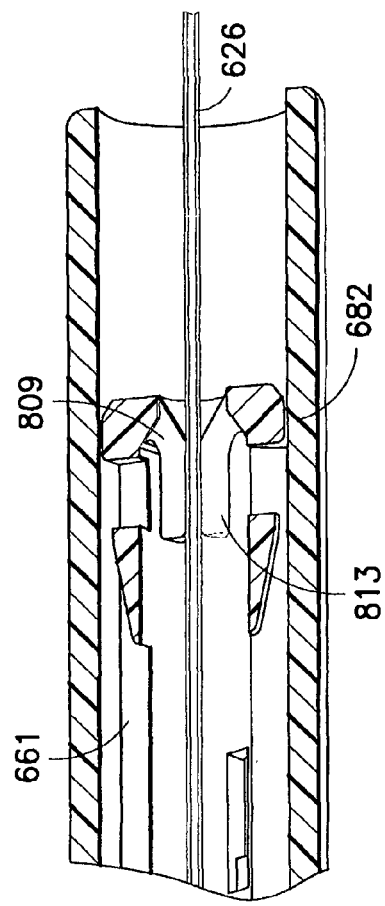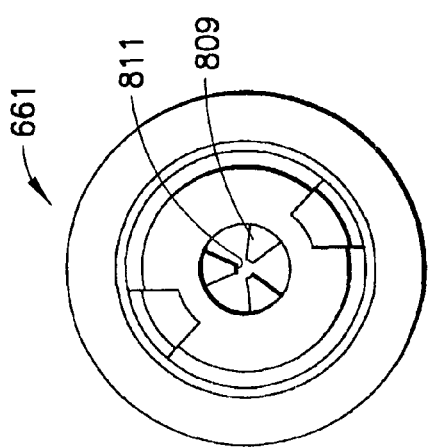

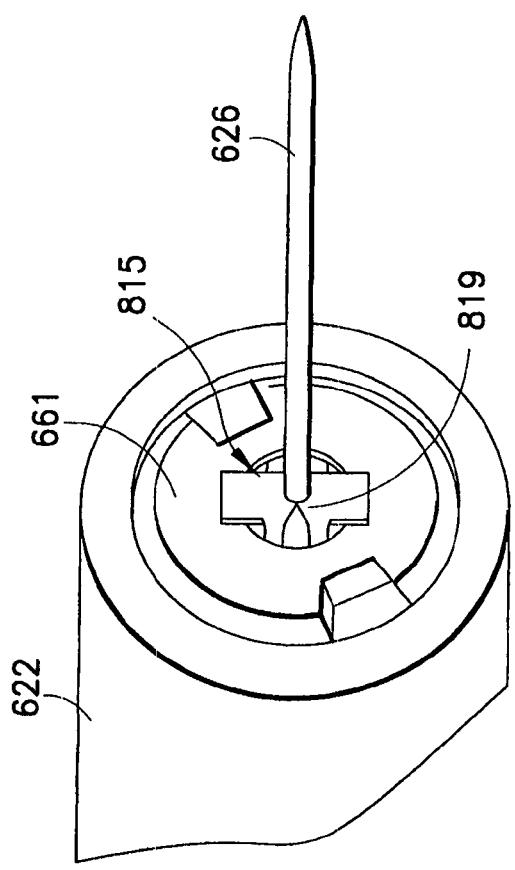
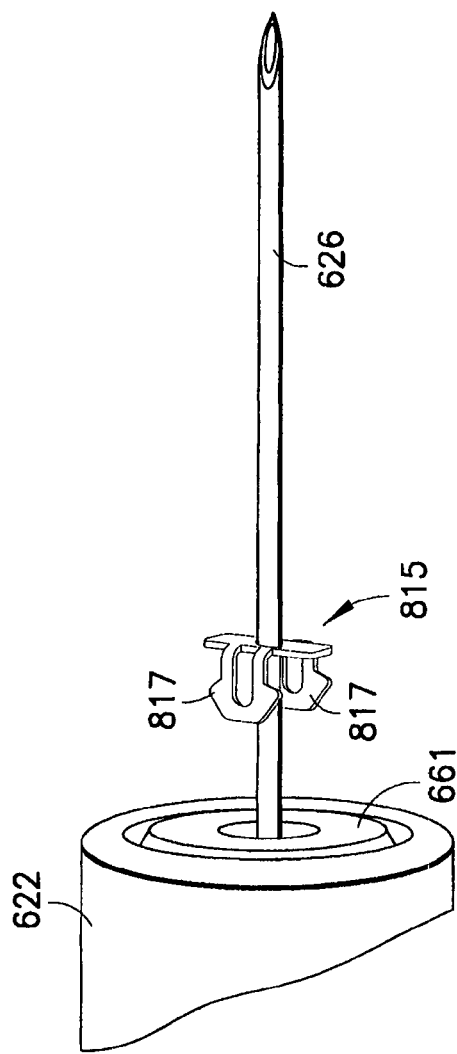

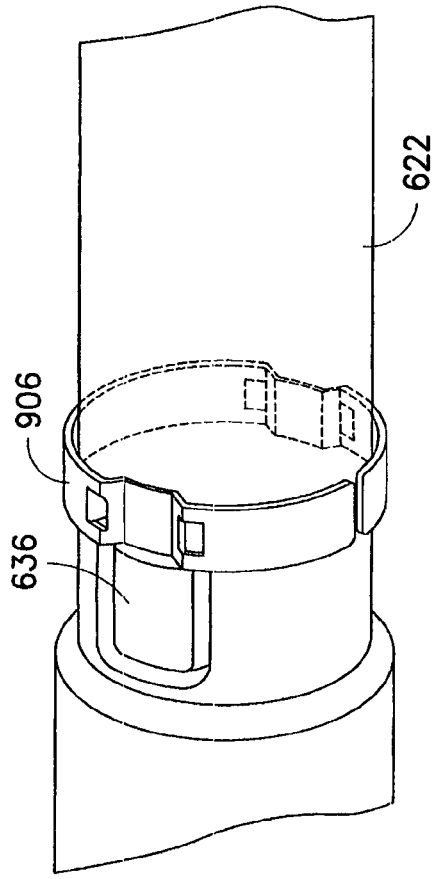
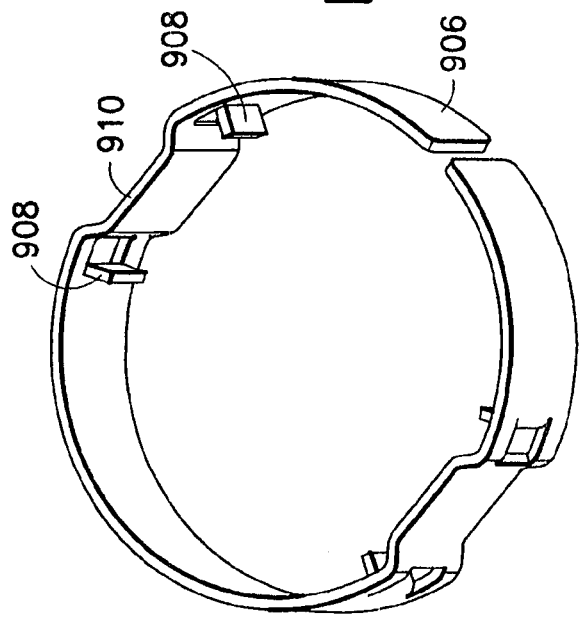
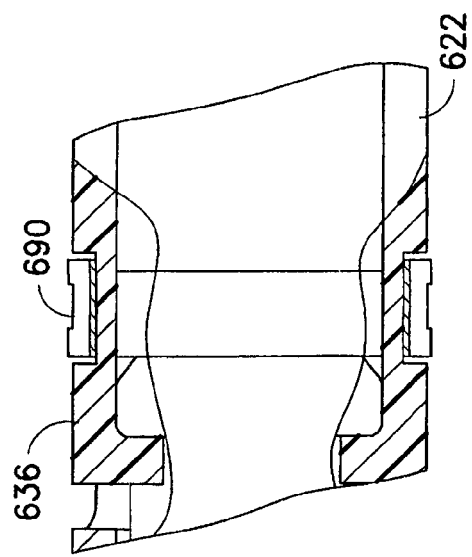

SAFETY SHIELD SYSTEM FOR A SYRINGE

BACKGROUND OF THE INVENTION

1. Field of the Invention

The present invention relates to a prefilled medical device for delivering a dose of medicament by injection and having an integral shield system for preventing accidental needle sticks after use.

2. Description of the Related Art

Syringes used for the delivery of medicaments to patients are well known. Oftentimes syringes are prefilled with a dosage of a medicament or other substance by a pharmaceutical manufacturer and then distributed to end users such as health care professionals or patients for administration of the prefilled medicament. Such syringes typically include a cylindrical hollow barrel which may be formed of a glass or plastic material and which may contain the medicament. One end of the barrel is fitted with a fixed or removable hollow needle, and the other end of the barrel receives a plunger having a stopper which is slidable with respect to the barrel for delivery of the medicament to the hollow needle, i.e., to urge the medicament toward and out of the needle. A syringe assembly, which typically includes the above-described components, is usually stored with a removable needle cover which protects the needle from damage during storage and handling. Prior to use, the needle cover is removed to expose the needle.

To prevent a syringe user and, in particular, a health care professional from inadvertent sticks by the needle after use of the syringe on a patient, the syringe assembly may incorporate a safety shield which forms a guard to cover the needle after use. Some such shields are spring activated for imparting a telescoping-like deployment action to the safety shield. Certain attributes to be considered in such syringe assemblies are that the shield should be intuitive and easy to use, should preferably provide consistent and reliable shield deployment, and should be operable with one hand. Other attributes are that such syringe assemblies require no change in current medicament delivery techniques, allow for dose adjustment, are preferably autoclavable, and allow for the inspection of contents before and after activation of the shield. Moreover, the use of the shield must not detrimentally affect processing and filling of the syringe at the pharmaceutical company, the assembly (i.e., syringe assembly and safety shield) must be easy to manufacture, must prevent accidental activation, and must limit the possibility of incurring cosmetic or structural damages.

SUMMARY OF THE INVENTION

The present invention relates to a medical device including a syringe assembly and incorporating a safety shield for covering the needle of the syringe assembly after administration of a dosage of medicament. The safety shield is automatically activated upon insertion of the needle of the syringe to a medicament delivery depth in a patient.

According to the present invention, the medical device for delivering a medicament to a patient includes a syringe having a barrel with a forward end and a rear end and defining a reservoir within which the medicament may be contained. As used herein, the term "forward," when used to describe the medical device and its various parts, refers to a part of the device that is closer to the patient. As used herein, the term "rear" or "rearward," when used to describe the medical device and its various parts, refers to a part of the device that is closer to the health care professional using the medical device. A needle or needle cannula (those terms being used interchangeably herein) having a forward tip is provided proximate the forward end of the barrel and is in fluid communication with the reservoir. A hub is connected to or provided on the barrel. A shield is movably mounted on the hub at a first position in which a part of the needle cannula is contained within the shield and, preferably, the tip of the needle cannula is not contained within the shield. An urging member is arranged between the hub and the shield for urging the shield toward the first position. The urging member may be, by way of non-limiting example, a coil spring, and is arranged on an exterior of the hub. The shield is movable from the first position to a second position against the influence or urgency of the urging member when the needle cannula is inserted into a patient for delivery of the medicament by interaction with the patient's skin. After delivery of the medicament, the shield is moveable from the second position to a third position, by the urgency of the urging member, upon removal of the needle cannula from the patient. When the shield is in the third position, the forward tip of the needle cannula is covered by the shield by a sufficient amount to prevent the tip of a finger from contacting the needle tip. As explained below, the shield may be secured in the third position to prevent the needle from being exposed after use.

A cover sleeve is mounted on the hub or the barrel and covers the portion of the urging member that extends between the shield and the hub in each of the first, second, and third positions of the shield. The cover sleeve may include a retainer arranged proximate a front end of the cover sleeve for interacting with a structure on the shield and blocking forward movement of the shield when the shield is in the third position. This feature prevents the shield from being removed from the device. The cover sleeve may additionally or alternatively include a projection between the two ends thereof for interacting with a resilient portion of the shield for blocking rearward movement of the shield when the shield is in the third position. The cover sleeve and shield may further include complementary interacting structures for preventing rotation of the shield relative to the cover sleeve when the shield is in the third position.

The hub may include a needle guide arranged proximate a forward end thereof. The needle guide may be formed unitarily as one piece with the hub and may also define a guide hole for radially supporting the needle cannula. Alternatively, the needle guide may comprise a separate piece having catches for forming a connection with the hub and a grip portion for providing radial support to the needle when the needle guide is connected to the hub.

The hub defines a track arrangement having an entry track and a lock-out track. The shield includes a pin mounted on a lever arm which is guidably received in the track arrangement. The entry track and the lock-out track are joined at an intersection. The pin is guided by the entry track when the shield moves from the first position to the second position and the pin is guided by the lock-out track when the shield moves from the second position to the third position.

The flexible arm may include a recess for reducing a force required to flex the lever arm. Alternatively, the flexible arm may include a spine along its axial length to increase a strength of the flexible arm. Ideally, the flexible arm includes both a recess at the junction of the flexible arm with the shield to reduce the force required to flex the arm when locking into the third position, and a spine along the flexible arm to increase the strength of the flexible arm in compression.

The medical device of the present invention may also include a locking device for locking the shield in the third position. The locking device may comprise an element that is similar to the blocking element having an inclined surface for facilitating movement of the pin in one direction, i.e. along the lock-out track to a fully-deployed position of the shield, and blocking movement of the pin in the reverse direction. The pin may have a tangentially inclined face interacting with the locking device when the shield is in the third position.

The lock-out track may extend parallel to the longitudinal axis of the medical device and the entry track may extend at least partially in the circumferential direction such that the shield rotates with respect to the longitudinal axis as the shield moves from the first position to the second position. Alternatively, the entry track may extend parallel to the longitudinal axis of the medical device and the lock-out track may extend at least partially in the circumferential direction such that the shield rotates with respect to the longitudinal axis as the shield moves from the second position to the third position. As a further alternative, both the entry track and the lock-out track may extend at least partially in the circumferential direction, such that the shield rotates as it moves from the first position to the second position and from the second position to the third position.

The cover sleeve may include a narrowed cylindrical portion for receiving a needle cover. The needle cover and the narrowed cylindrical portion may include corresponding structures for securing the needle to the needle cover during storage and/or for facilitating axial movement of the needle cover in response to twisting of the needle cover.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 1 is an exploded perspective view of the components of a medical device according to an embodiment of the present invention;

FIG. 2 is a perspective view of the assembled medical device of FIG. 1;

FIG. 4 is a perspective sectional view of a shield of the medical device of FIG. 1 along a longitudinal axis of the shield;

FIG. 5 is a perspective view of a forward end of a syringe barrel of the medical device of FIG. 1;

FIG. 9 is a sectional view of the entry track in the syringe barrel of the medical device of FIG. 1;

FIG. 10 is a sectional view of the lock-out track in the syringe barrel of the medical device of FIG. 1;

FIG. 11 is a longitudinal sectional view of the medical device of FIG. 1 after use;

FIG. 16 is a perspective cross-sectional view of another embodiment of a medical device according to the present invention;

FIG. 17 is a perspective view of a hub of the shield assembly of FIG. 16;

FIG. 18 is a perspective cross-sectional view of the device of FIG. 16 with a cover sleeve retainer;

FIG. 22 is a longitudinal cross-sectional view of an embodiment of a cover sleeve;

FIG. 23 is a perspective view of a front of the cover sleeve of FIG. 22;

FIG. 24 is a side view of a shield for use with the cover sleeve of FIG. 22;

FIG. 25 is a perspective view of the shield of FIG. 24 inserted in the cover sleeve of FIG. 22;

FIG. 29 is a longitudinal cross-sectional view of the hub of FIG. 16;

FIG. 30 is a front view of the hub of FIG. 29 with a needle retainer;

FIG. 31 is a longitudinal cross-sectional view of a hub as in FIG. 29 which includes an inner cylinder;

FIG. 32 is a front view of the hub of FIG. 29 having another embodiment of a needle retainer;

FIGS. 33 and 34 are longitudinal sectional views of a hub with the needle retainer of FIG. 32;

FIG. 35 is a perspective view of the medical device of FIG. 16 with another embodiment of a needle retainer;

FIG. 36 is a side view of the needle retainer of FIG. 35 before connection to the hub;

FIG. 43 is longitudinal cross-sectional view of a shield including a reinforcement collar;

FIG. 44 is a perspective view of the reinforcement collar and shield of FIG. 43;

FIG. 45 is a perspective view of the reinforcement collar of FIG. 43;

DETAILED DESCRIPTION OF THE PRESENTLY PREFERRED EMBODIMENTS

Figure 3:
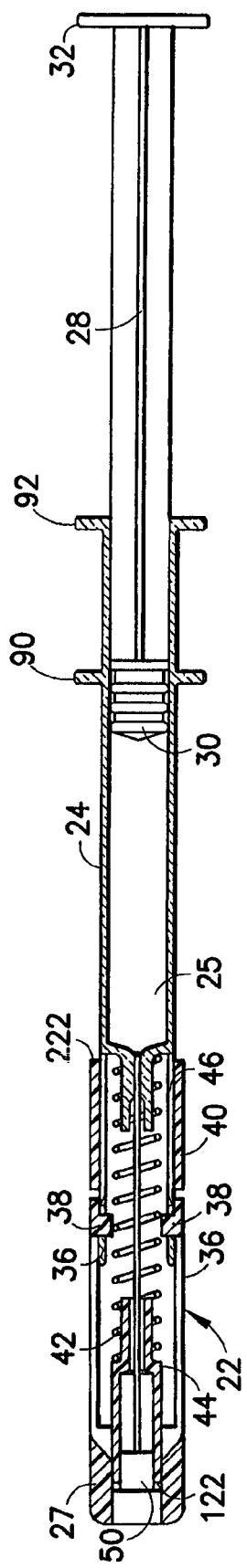
FIG. 3 is a longitudinal cross-sectional view of the medical device of FIG. 1 in a state prior to use.

FIGS. 1-3 show a medical device 10 for delivery of a medicament into a patient constructed in accordance with an embodiment of the present invention. As used herein, the term "medicament" is intended to refer to any drug substance, vaccine, or other liquid substance that is injected into the patient. The medical device 10 includes a syringe 20 which can be prefilled with the medicament to be delivered, and a shield 22 which surrounds a front end of the syringe 20.

The syringe 20 includes a cylindrical barrel 24 defining a reservoir 25 (see FIG. 3) within which the medicament may be held prior to use of the medical device 10. The syringe 20 also includes a needle cannula 26 having a forward tip 126 and a rearward end 226 in fluid communication with the reservoir 25. The needle cannula 26 may be permanently connected to a front end of the barrel 24 using an adhesive, glue, interference fit or other known or hereafter developed material or technique, or it may be detachable from the barrel such as for example, using a luer-type connection. A front section 60 of the barrel 24 defines tracks 62, 64 in a surface thereof, preferably an outer surface thereof, which interact with the shield 22 as explained in detail below. The barrel 24 is preferably made of plastic. However, the barrel 24 may also be made of glass. In an alternative embodiment, the barrel 24 may be made of glass with the front section 60 made of plastic. Other materials and combinations of materials may be used to make the medical device 10 of the present invention, in accordance with the disclosure provided herein. A plunger rod 28 has a first end inserted in the barrel 24 with a stopper or piston 30 arranged on the first end that is movable with the plunger 28 into and within the barrel 24. A second end of the plunger rod 28 includes a thumb pad 32 for receiving pressure from the user's thumb for moving the piston 30 into and within the barrel 24. Finger rests 90, 92 on the barrel in the form of flanges provide ergonomic grips for holding the medical device 10 during insertion of the needle cannula 26 and during the application of medicament delivery force to the thumb pad 32. Although these finger rests 90, 92 are depicted as flanges, any other designs may be used such as, for example, radial projections. In addition, a single or a plurality of finger rests may be provided. The finger rest(s) may be formed unitarily with the barrel 24, or as a separate component that may be secured on or to the barrel 24.

As further shown in FIGS. 1 and 2, a removable needle shield 27 is disposed over the needle cannula 26 on the front end of the shield 22 to protect the needle from damage during the handling of the medical device 10, and to protect users from being stuck by the needle prior to its intended use. The needle shield 27 preferably includes a pliable part 127 and a rigid part 227.

As described below, the shield 22 is movable from an initial or first position, in which the forward tip 126 of the needle cannula 26 extends beyond a front end 122 of the shield 22, to an intermediate or second position, and then from the intermediate position to a shielded or third position in which the forward tip 126 of the needle cannula 26 is contained within the shield body 22. An urging member 42, such as, for example, a coil spring or biasing arm, urges the shield forward relative to the barrel 24. Thus, the urging member 42 maintains the shield 22 in the first position prior to use, and urges or causes the shield 22 to move from the second position to the third position.

The various component parts of the inventive medical device 10 will now be discussed in further detail. The shield 22 is depicted in FIG. 4 and is generally cylindrically-shaped. The front end 122 of the shield defines a channel passage or guide hole 50 through which the needle cannula 26 extends when the shield 22 is in the first and second positions. The shield 22 also includes an upper and lower lever arm 36 running longitudinally along the outer surface of the shield 22, preferably defined in or on an outer surface thereof (only a free end of the upper lever arm 36 is visible in FIG. 4). The free end of each of the lever arms 36 includes a pin 38 extending radially inward from an outer surface of the shield 22. Although two lever arms 36 are shown in the preferred embodiment, the shield 22 may include one or a plurality of lever arms 36. A seat 44 is defined proximate the front end 122 for receiving an end of the urging member 42 as described below.

Figure 6:
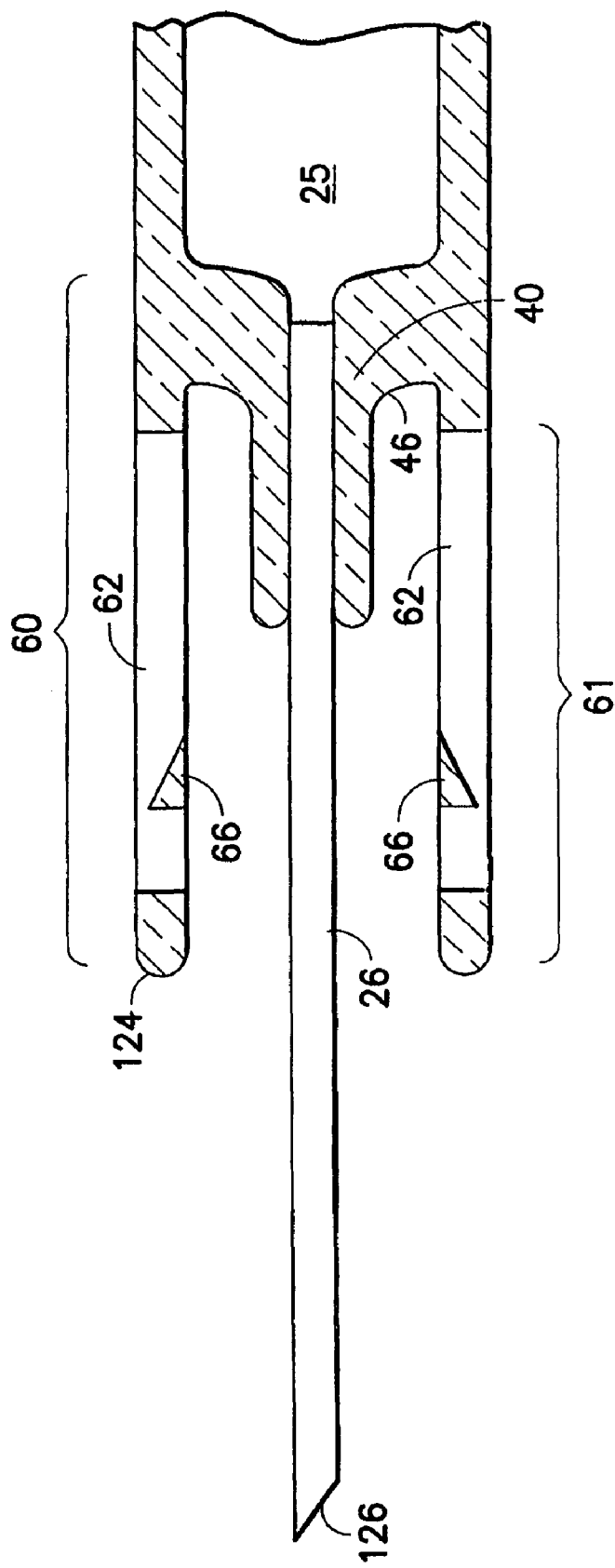
FIG. 6 is a partial longitudinal sectional view of the forward end of the syringe barrel of FIG. 5.

The front end portion 60 of the barrel 24 is shown in FIGS. 5 and 6. The front end portion 60 includes a needle holder 40 in and to which the needle cannula 26 is mounted, and a cylindrical portion 61 arranged in front of the reservoir 25 and about the needle holder 40 and part of the needle cannula 26. The cylindrical portion 61 may be unitarily defined with the barrel 24, or it may be added to the front of the syringe barrel 24 using an adhesive or other permanent connection. The connection may also be, by way of non-limiting example, made by one of press fitting, spin welding, heat stake, or threading. The front end portion 60 defines two intersecting pair of tracks 63 on the cylindrical portion 61 corresponding to the two lever arms 36 (only one pair of tracks 63 is visible in FIG. 5). Each pair of tracks 63 comprises an entry track 64 and a lock-out track 62 which intersect with each other. The pin 38 of each lever 36 is received in one of the lock-out and entry tracks 62, 64 of a corresponding one of the pair of tracks 63. In the initial position of the medical device shown in FIGS. 1-3 in which the front tip 126 of the needle cannula 26 extends past the front end 122 of the shield 22, the pins 38 are located in end areas 72 (see FIG. 5) of the entry track 64 proximate the front end 124 of the barrel 24. The urging member 42 is arranged between a front facing surface 46 (see FIG. 6) of the needle holder 40 and the seat 44 (see FIG. 4) arranged at the front end 122 of the shield 22 for urging the pins 38 against the front surfaces 65 of the entry tracks 64 proximate the end areas 72 thereby maintaining the shield 22 in the first position prior to use of the medical device 10. Accordingly, the interaction of the pins 38 and the front surfaces 65 of the entry tracks 64 prevents the shield 22 from sliding off of the front of the barrel 24 under the influence of the urging member 42.

Figure 7:
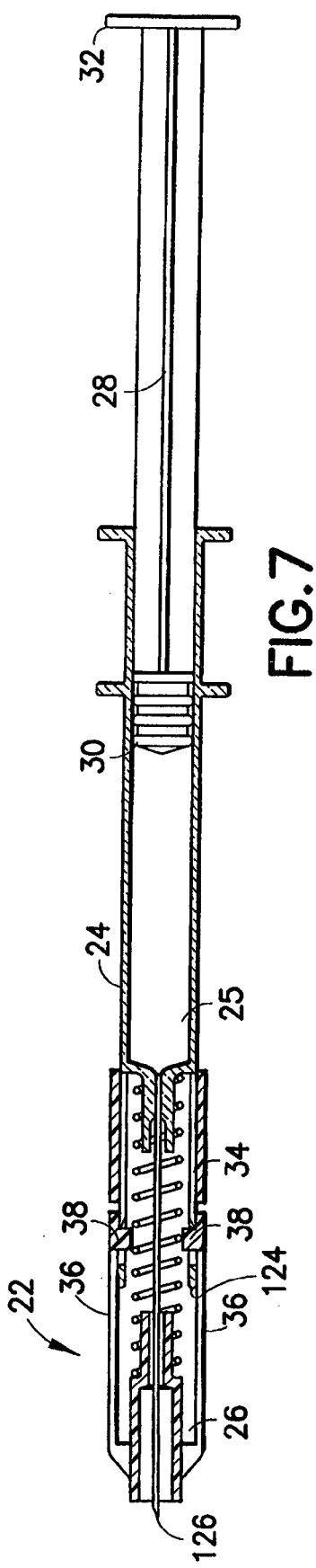
FIG. 7 is a longitudinal sectional view of the medical device of FIG. 1 in a ready to use state.

Prior to use of the medical device 10, the removable needle shield 27 is separated from the medical device 10. At this stage, the shield 22 is in the position, as shown in FIGS. 3 and 7, in which the pins 38 are in the end areas 72 of the entry tracks 64. As depicted in FIG. 7, a portion of the needle cannula 26 proximate the forward tip 126 is exposed when the shield 22 is in the first position. However, the forward tip 126 is not required to be exposed in this position. Therefore, the forward tip 126 may alternatively be covered by or contained within the shield 22 when it is in the first position.

Figure 8:
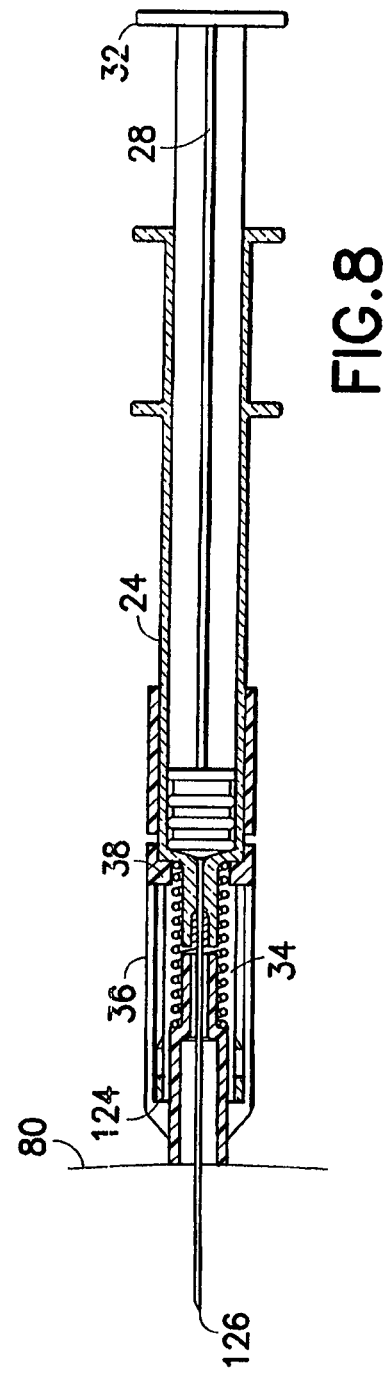
FIG. 8 is a longitudinal sectional view of the medical device of FIG. 1 during use.

As the needle cannula 26 is inserted into a patient to deliver the medicament, the front end 122 of the shield 22 contacts the skin 80 of the patient, as depicted in FIG. 8. As the needle cannula 26 continues to be inserted into the patient, contact between the patient's skin 80 and the front end of the shield 122 causes the shield 22 to move in a rearward direction (i.e., toward the rear end of the medical device 10), until the needle cannula 26 is fully inserted in the patient as shown in FIG. 8. During the movement of the shield 22, each of the pins 38 moves along a respective entry track 64. During this movement, each pin 38 moves from end area 72 over a one-way entry step 68 and into a central position 74 of the lock-out track 62, which is approximately located at the intersection of the entry track 64 and lock-out track 62. This path is shown in FIG. 9 which is a sectional view along the longitudinal axis of the entry track 64. As each pin 38 passes over the one-way entry step 68, it moves along an inclined portion 82 and the lever arm 36 resiliently flexes radially outward in a direction traverse to the axis of the medical device 10. Once the pin 38 passes over the one-way entry step 68, the lever arms 36 return to their original positions and the pin 38 is, at that point, located in the central position 74 of the lock-out track 62 with the shield 22 being in the second position. When the pin 38 passes the one-way entry step 68 and enters the central position 74 of the lock-out track 62, the shield 22 is actuated and a blocking surface 84 of the one-way entry step 68 blocks reentry of the pin 38 into the entry track 64. Even though the shield 22 is actuated in this position, the needle cannula 26 may be inserted further into the patient so that the shield 22 is pushed further back against the force of the urging member 42 and onto the barrel 24. As this occurs, the pins 38 move toward the rear ends 76 of the lock-out paths 62. The second position of the shield 22 may be any position between the first and third positions. Thus, when the shield is in the second position, the pin 38 may be located at any position in the entry track 64 or lock-out track 62 that does not define or delineate the first or third positions.

After the medicament is delivered, the needle cannula 26 is removed from the patient. This provides clearance for the shield 22, whereupon the shield 22 is then urged, by the force of the compressed urging member 42, to a third position in which the shield body 22 extends beyond the forward tip 126 of the needle cannula 26. As shown in FIGS. 5 and 10, each lock-out path 62 also includes a one-way lock-out step 66 which has an inclined surface 86 and a blocking surface 88. The inclined surface 86 allows the pin 38 guided in the lock-out track 62 to move toward the forward end 78 of the lock-out track 62 as the shield 22 moves from the second position to the third position. When the shield 22 reaches the third position, the pin 38 is in the forward area 78 between the one-way lock-out step 66 and a forward end 89 of the lock-out track 62. The blocking surface 88 prevents the pin 38 from moving out of the forward end 78, thereby locking the shield 22 in the third position, as depicted in FIG. 11.

Figure 12:
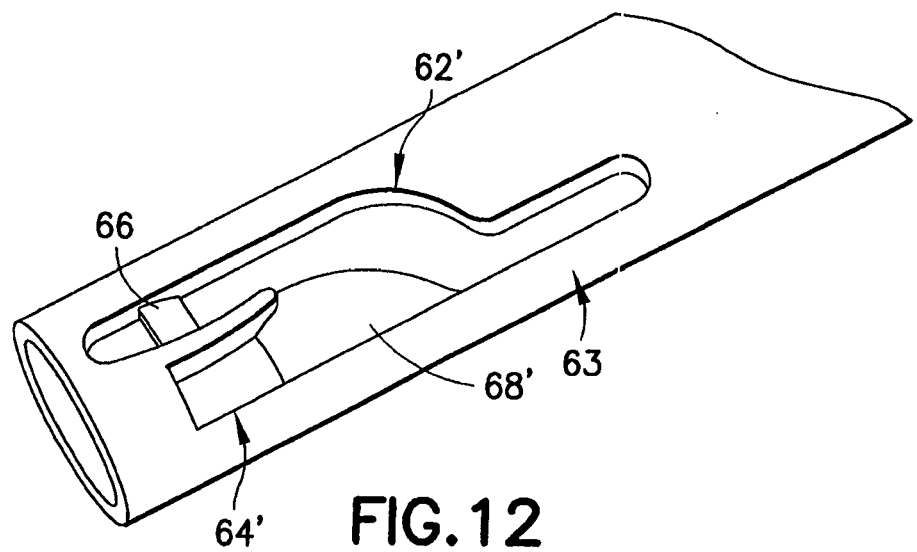
FIG. 12 is a perspective view of an alternative embodiment of the shield of the medical device according to the present invention.

In the embodiment of FIGS. 1-11, the entry track 64 is curved such that as the pin 38 is moved along the entry track 64 during insertion of the needle cannula 26 in the patient, the shield 22 is rotated about the longitudinal axis of the device 10 until the pin 38 enters the central area 74 of the lock-out track 62. The lock-out track 62 extends parallel to the longitudinal axis so that the shield does not rotate during movement of the pin in the lock-out track 62. In an alternative embodiment shown in FIG. 12, the entry track 64' is arranged parallel to the longitudinal axis of the shield so that the shield 22 does not rotate during insertion of the needle cannula 26 into the patient. Rather, the shield 22 rotates as the pin 38 moves between the entry track 64' and the lock-out track 62' during the withdrawal of the needle cannula 26 from the patient. In each of the embodiments of FIGS. 1-12, one of the entry track 64, 64' and the lock-out track 62, 62', extends parallel to the longitudinal axis of the device 10. However, there is no requirement that one of the tracks be parallel to the longitudinal axis of the device 10. Accordingly, both the entry and lock-out tracks may extend at an angle relative to the longitudinal axis of the device 10 such that the shield 22 rotates during movement from the first to the second position and from the second position to the third position.

Figure 13:
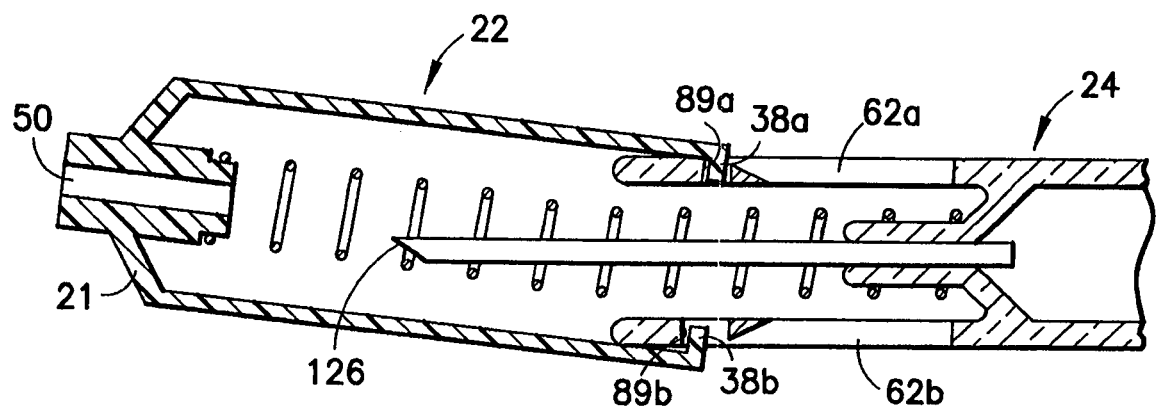
FIG. 13 is a partial longitudinal sectional view of a further embodiment of the shield and barrel according to the present invention.

FIG. 13 shows another alternative embodiment in which the end surfaces 89a, 89b of lock-out tracks 62a, 62b are axially offset from each other. When the shield 22 is in the third position, pin 38a first contacts the end surface 89a which causes the shield 22 to pivot about the initial point of contact at end surface 89a until the pin 38b rests on the end surface 89b (or until the shield 22 contacts the needle cannula), as shown in FIG. 13. In this position, the shield 22 is askew relative to the needle cannula 26 and the needle cannula 26 is not aligned with the hole 50 in the shield through which it was formerly inserted. This configuration further prevents inadvertent needle sticks because when the shield 22 is pressed toward the barrel 24, the forward tip 126 of the needle cannula 26 is not aligned with the hole 50 but, instead, contacts a front wall 21 of the shield 22 thereby maintaining the needle tip 126 within the shield 22. This embodiment may be used with or without the lock-out step 66 described above.

Figure 14:
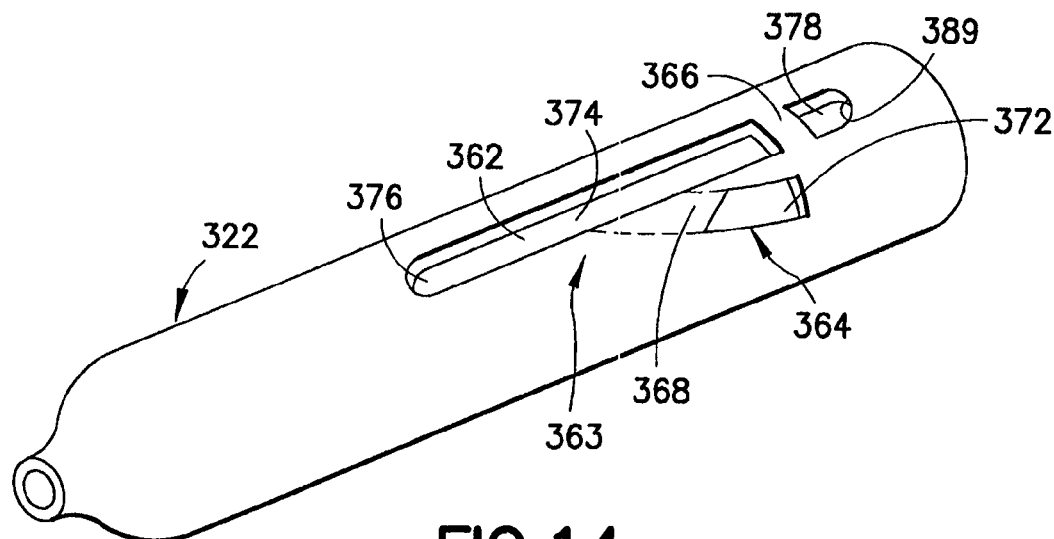
FIG. 14 is a perspective view of a shield according to yet another embodiment of the present invention.
Figure 15:
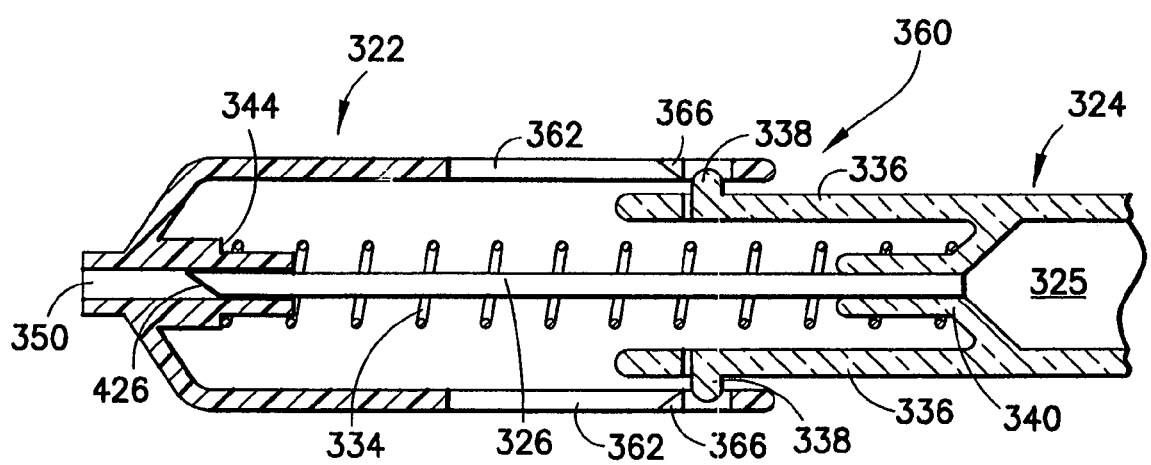
FIG. 15 is a partial longitudinal sectional view of the shield of FIG. 14 with the barrel of the syringe assembly.

FIGS. 14-15 show a further embodiment of the present invention in which pairs of tracks 363 are defined in or on a shield 322, each pair of tracks 363 including an entry track 364 and a lock-out track 362. A front portion 360 of a syringe barrel 324 includes lever arms 336 with radially outwardly extending pins 338 or projections which are received in the tracks 363. Similarly to the above embodiment disclosed in FIGS. 1-11, the shield 322 is arranged in a first position in which a forward tip 426 of a needle cannula 326 is exposed as shown in FIG. 7. In the first position of the shield 322, the pins 338 are in end areas 372 of the entry tracks 364. As the needle cannula 326 is inserted into a patient for delivery of the medicament, the shield 322 contacts the patient's skin which causes the shield 322 to move in a rearward direction against the influence of the urging member 334 such that the pin 338 is guided along the entry track 364 and over the inner surface of the step 368. The entry track 364 is similar to the entry track 64 shown in FIG. 9 and extends across the inner surface of the step 368 to the lock-out track 362 as indicated by the dotted lines in FIG. 14. Once the pins 338 enter the lock-out tracks 362, the steps 368 block reentry of the pins 338 into the entry tracks 364. The shield 322 may be pushed further rearward by continued forward movement of the needle cannula 326 into the patient until the pins reach the end areas 376. When the needle cannula 326 is removed from the patient, the urging member 334 urges the shield 322 forward until the pins 338 rest against end surfaces 389 of the lock-out tracks 362. As described above regarding lock-out step 66 in FIGS. 5 and 6, each lock-out track 362 includes a lock-out step 366 which allows pin 338 to move toward the end area 378 and blocks the pin 338 from moving out of the end area 378 once it has entered the end area 378.

A description of an exemplary usage of the medical device 10 of the present invention will now be provided with respect to FIGS. 1-11. It should be understood by a person of ordinary skill in the art that the following description is provided as an illustrative and non-limiting example. The health care professional receives the inventive medical device 10 prefilled with a desired dosage of medicament. Immediately prior to use, the needle shield 27 is removed and the forward tip 126 of the needle cannula 26 is exposed. The health care professional pierces the patient's skin with the forward tip 126 of the needle cannula 26 and inserts the needle cannula 26 to the proper penetration depth. The shield 22 is in the first position prior to use and when the needle cannula 26 is first inserted into the patient's skin. As the needle cannula 26 is further inserted into the patient, the shield 22 moves rearward in the direction of the barrel 24 from the first position to the second position. This causes charging or compression of the urging member 42. During this movement, the pin 38 of the shield 22 is guided in the entry track 64, over the step 68 and into the lock-out track 62 at which point the shield 22 is in the second position. As the needle cannula is further inserted, the shield is pushed further onto the barrel and the pin 38 is guided in the lock-out track 62 toward end area 76. Preferably, but not necessarily, this results in complete charging or compression of the urging member 42.

Once the needle cannula 26 is fully inserted into the patient, the health care professional depresses the thumb pad 32 to cause the plunger rod 28 and piston 30 to move within the reservoir 25. As the plunger rod 28 and piston 30 are moved into the reservoir, the medicament is caused to be expelled from the reservoir 25, through the needle cannula 26, and into the patient. After delivery of the medicament, the health care professional withdraws the needle cannula 26 from the patient. As the needle cannula is withdrawn, the urging member urges the shield 22 forward until the shield 22 reaches the third position when the needle cannula 26 is completely withdrawn and in which the shield 22 covers the forward tip 126 of the needle cannula 26, thus preventing undesired and inadvertent exposure of the health care professional to the contaminated forward tip 126. The used medical device may then be disposed of in a suitable sharps disposal container.

FIGS. 16-17 show yet another embodiment of a medical device 600 of the present invention in which a syringe barrel 624 defines a reservoir 625 and includes a needle cannula 626 having a rearward end in fluid communication with the reservoir 625. A hub 661 comprising a cylindrical extension is arranged on the syringe barrel 624 in front of the reservoir 625. As in the previous embodiments, the syringe barrel 624 may be made of glass or plastic. The hub 661 is made of plastic and is connected to the syringe barrel 624 using adhesive, glue, interference fit, spin welding, heat stake, threading, luer lock or other known or hereafter developed material or technique. The hub 661 may also be unitarily formed with the barrel 624. The hub 661 includes two pairs of tracks 663, each including an entry track 664 and a lock-out track 662. A shield 622 is arranged so that it surrounds at least a portion of the hub 661 and is axially movable relative to the hub 661. An urging member 642, such as, for example a coil spring or biasing arm, urges the shield 622 forward relative to the hub 661. In the embodiment of FIGS. 16 and 17, the urging member 642 is arranged external to the hub 661. A seat 644 is arranged proximate a rear end of the shield 622 for receiving a forward end of the urging member 642.

Figure 27:
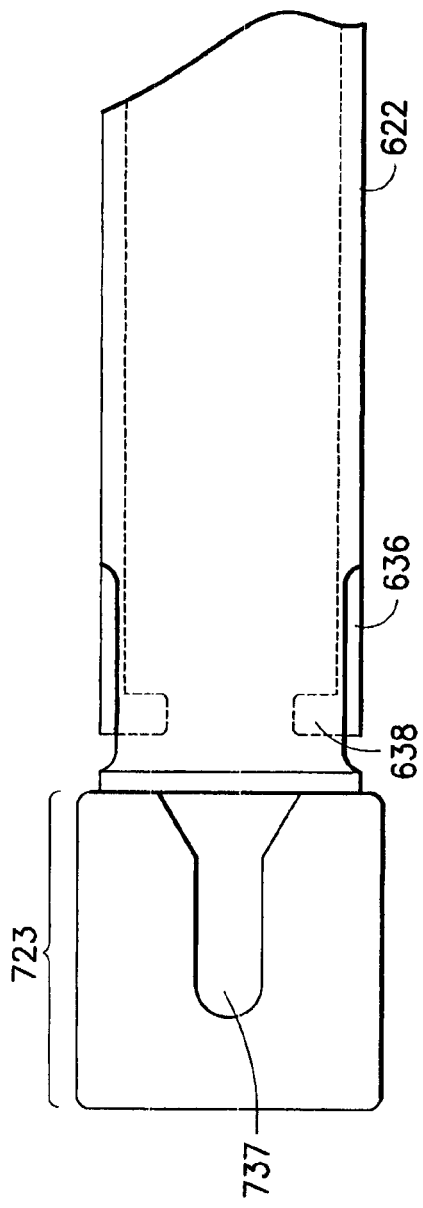
FIG. 27 is a longitudinal cross-sectional view of a shield for use with the cover sleeve of FIG. 26.

Similarly to the above-described embodiments of FIGS. 1-11, the shield 622 includes upper and lower lever arms 636 (see, e.g., FIG. 27). The free end of each lever arm 636 includes a pin 638 (see FIG. 27). As in the previous embodiments, the shield 622 may include one or more of the lever arms 636. The pin 638 of each lever arm 636 is received in one of the lock-out and entry tracks 662, 664 of a corresponding one of the tracks 663. The lock-out and entry tracks 662, 664 are similar to the lock-out and entry tracks 62, 64 shown in FIG. 5. The entry track 664 extends across an outer surface of a step 668 to the lock-out track 662. The interaction of the pins 638 and tracks 663 is in accordance with the above description of pin 38 and track 63. The tracks 662 and 664 may alternatively be arranged similarly to the tracks 62' and 64' shown in FIG. 12.

As described in the previous embodiments, the shield 622 is in a first or initial position prior to use of the medical device 600 in which the pins 638 of the lever arms 636 are in the entry tracks 664. A forward tip of the needle cannula may or may not be covered by the shield when it is in the first or initial position. After the needle cover 627 is removed and the needle cannula is inserted in the patient, the shield 622 contacts the patients skin and is pushed toward the syringe barrel 624 against the influence of the urging member 642. During this movement, the pins 638 move over entry steps 668 into a second or central position in lock-out tracks 662. When the needle cannula 626 is removed from a patient, the force of urging member 642 pushes the shield so that the pins 638 move along the lock-out track 662 over lock-out steps 666 to the third or shielded position in which the shield extends past the end of the needle cannula 626. Lock out step 666 is similar to lock out step 66 in FIGS. 5 and 10.

The embodiment of FIGS. 16-17 further includes a cover sleeve 682 surrounding the hub 661 and at least part of the shield 622. The cover sleeve 682 ensures that the urging member 642 is always surrounded to protect against inadvertent obstruction by a user during operation of the device. In FIG. 16, the cover sleeve 682 is shown as being connected to a portion of the syringe barrel 624. However, the cover sleeve may also be directly connected to the hub 661. The cover sleeve 682 may be connected to either the syringe barrel 624 or the hub 661 by snap fit connection 686 and may include seal rings 687. The cover sleeve 682 may also be connected using adhesive, glue, interference fit, spin welding, heat stake, threading or other known or hereafter developed material or technique. A needle shield 627 (described in more detail below) may be connected at front end of the cover sleeve 682. Furthermore, sterility barrier 688 may be applied to the connection between the needle shield 627 and cover sleeve 682.

As shown in FIG. 18, a retainer 683 may be arranged at a front end of the cover sleeve 682. The retainer 683 interacts with a forward facing surface 725 (described in more detail below) on the shield 622 to prevent forward movement of the shield when the shield is in the third position, thereby preventing separation of the shield from the cover sleeve 682 and the hub 661. The retainer 683 may comprise one or more radially inward projections proximate the forward end of the cover sleeve 682. Instead of individual projections, the retainer 683 may comprise a continuous or interrupted radially inward projecting annular ring.

Figure 19:
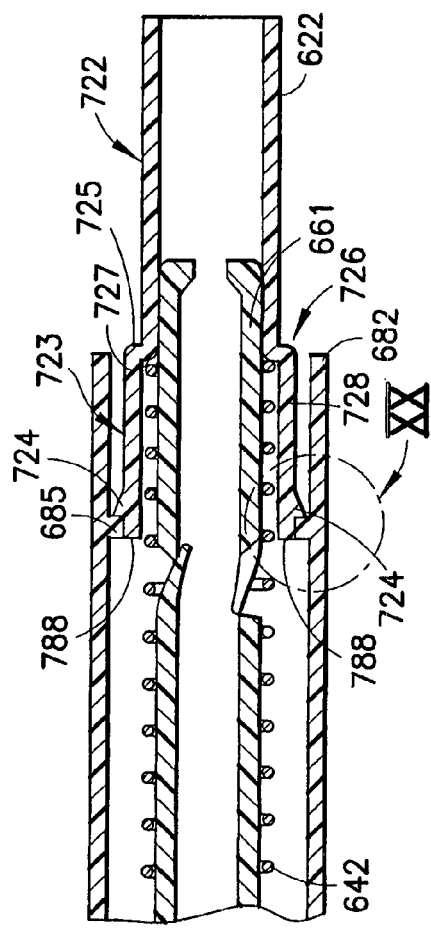
FIG. 19 is a partial longitudinal cross-sectional view of the device of FIG. 16 with a ring for preventing rearward movement of the shield.

FIG. 19 shows a radially inward projecting ring 685 arranged at a distance from a front end of the cover sleeve 682. The ring 685 may be continuous or interrupted. The ring 685 interacts with a rear facing projection 724 of the shield 622 to prevent the shield from moving rearward when the shield is in the third position. Accordingly, the ring 685 may be used instead of or in addition to a lock out step 666 in the lock out track 662.

FIG. 19 further shows that the shield 622 includes a forward portion 722 and a rearward portion 723 which has a larger diameter than the forward portion 722. A transition area between the forward and rear portions includes a shoulder 726 having the forward facing surface 725 on an exterior surface of the shield 622 and a rearward facing surface 727 on an interior surface of the shield 622. The forward end of urging member 642 interacts with the rearward facing surface 727 such that the rearward facing surface 727 comprises the seat 644 in FIG. 16.

Figure 20:
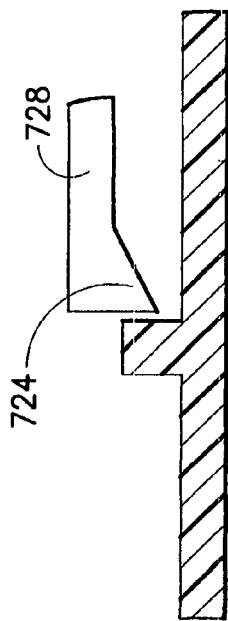
FIG. 20 is a enlarged cross-sectional view of area XX in FIG. 19 showing a retainer for the shield.

The rearward portion 723 of the shield 622 may be cylindrical. Alternatively, the rearward portion 723 of the shield may include a plurality of circumferentially spaced resilient legs 728, each including one of the projections 724. The legs 728 are urged inwardly toward the needle cannula 626 as the projections 724 pass over the ring 685 when the shield is moved along the lock-out track toward the third position. The legs 728 resiliently snap radially outward once the projection 724 pass over the ring 685 and the shield 622 is in the third position. The rear ends of the projections 724 interact with the ring 685 in the third position of the shield 622 so that the shield 622 is prevented from moving rearward. As shown in FIG. 19, the projection 724 is positioned such that a portion 788 of the leg 728 extends past the projection 724 to the free end of the leg 728. This portion 788 interacts with a radially inner side of the ring 685 to stabilize the shield 622 when the shield is in the third position, as shown in FIG. 19. However, the projections 724 may alternatively be arranged at the free ends of the legs 728, as shown in FIG. 20.

Figure 21:
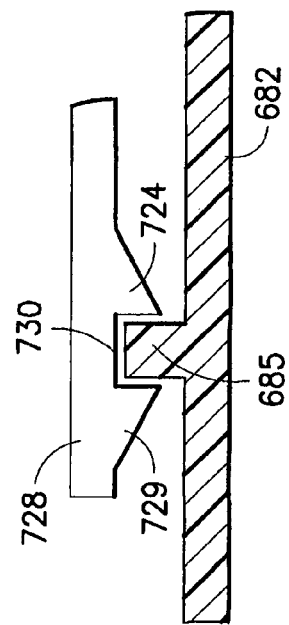
FIG. 21 is an enlarged cross-sectional view of the area XX in FIG. 19 showing an additional projection on the retainer for the shield.

In a further embodiment shown in FIG. 21, the legs may further comprise a forward facing projection 729. A gap 730 is defined between the projections 724, 729. The ring 685 is received in the gap 730 when the shield 622 is in the third position so that the shield 622 is prevented from moving forward by projection 729 and prevented from moving backward by projection 724.

FIGS. 22 and 23 show an embodiment in which the cover sleeve 682 includes both the retainer 683 and the ring 685. In this embodiment, the retainer 683 is not ring-shaped but is configured as a small projection. In addition, ring 685 is not continuous and includes a gap 686 which allows the lever arm 636 to flex outward, for example, when the pins 638 are moved over steps 668 (see FIG. 17). In FIG. 24, the forward portion 722 of the shield 622 additionally includes an axially extending projection 731 proximate the shoulder 726 which interacts with a circumferential side of retainer 683 to prevent rotation of the shield when the shield is in the third position. FIG. 25 shows two projections 731, one preventing clockwise movement and the other preventing counter-clockwise movement of the shield 622 relative to the cover sleeve 682.

Figure 26:
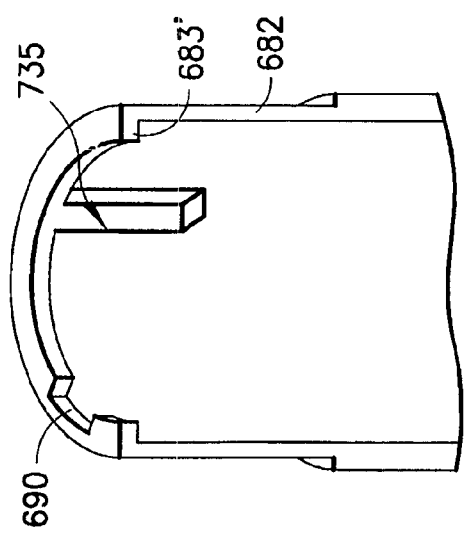
FIG. 26 is a perspective cross-sectional view of a cover sleeve according to another embodiment.

FIGS. 26 and 27 show another embodiment for preventing rotation of the shield. In FIG. 26, the cover sleeve 682 includes an axially extending rib 735 formed on an inner surface of the sleeve and extending along a length from a position proximate the retainer 683' toward the rear end of the cover sleeve 682. The rearward portion 723 of the shield 622 defines a slot 737 on an exterior surface in which the axially extending rib 735 engages when the shield is moved to the third position. The shield 622 is prevented from rotating when the rib 735 engages the slot 737. In this embodiment, the positions of the rib 735 and slot 737 must be coordinated with the positions of the lock-out track 662 (not shown in FIG. 27) and pin 638 so that the rib is aligned with the slot when the shield is moved to the third position.

Figure 28:
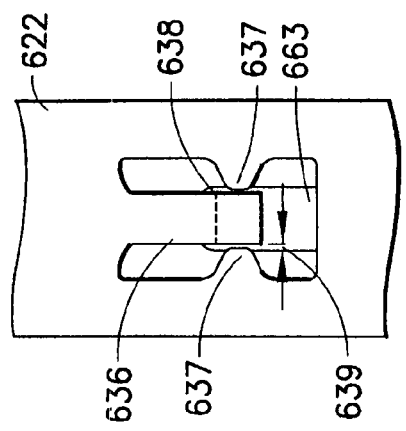
FIG. 28 is a side view of shield including projections for preventing rotation of the shield.

FIG. 28 shows an embodiment in which the pins 638 in the tracks 663 and the lever arms 636 are used to prevent rotation of the shield. In this embodiment, the shield 622 includes lateral supports 637 facing the lateral sides of the free end of the lever 636. The lateral supports minimize the tangential clearance 639 between the lateral sides of the free end of the lever 636 and the shield 622. This increases the force required to take the pin 638 out of the tracks 663.

FIGS. 29 and 30 show that the hub 661 may include a stabilizer 805 to provide radial support to the needle cannula 626. The stabilizer 805 includes a conical, frustum-shaped or funnel-shaped member connected at a front end of the hub 661 and defining a guide hole 650 which substantially corresponds to a diameter of the needle cannula 626, thereby providing added support to the needle cannula 626, which is necessarily long to pass through the hub 661 and to the patient. Although the described embodiment discloses a conical-shaped stabilizer, the stabilizer may take any shape or form. The important characteristic is that the stabilizer be a structure that is capable of providing support to the needle cannula 626. As further shown in FIG. 31, an inner cylinder 807 may be connected to the stabilizer 805 to provide additional support along the length of the needle cannula 626, the inner cylinder extending from the stabilizer 805 toward the syringe barrel 624.

Instead of being funnel-shaped, the stabilizer may include plural legs or elements 809 extending radially inward from the front end of the hub 661 and forming a partial funnel as shown in FIGS. 32-34. The inner ends 811 of element 809 each provide radial support to the needle cannula 626. Although three elements 809 are shown, two or more elements may be used to accomplish the result. Although a partial funnel-shape is disclosed, the elements may include any shaped structure capable of providing support for the cannula. In addition, each of the elements 809 may further comprise an axially extending portion 813 as shown in FIGS. 33 and 34.

FIGS. 35 and 36 shown another stabilizer 815 formed of stamped metal that is bent to include two catches 817 designed to form a snap-fit or friction-fit connection at the front end of the hub 661. The stabilizer 815 further comprises a gripping section 819 through which the needle cannula 626 extends. The gripping section 819 grips and provides radial support for the needle cannula 626 when the two catches 817 are inserted into the hub 661. Instead of a stamped metal, the stabilizer may comprise a machined or formed metal or plastic part having the above-described catches and gripping section.

Figure 37:
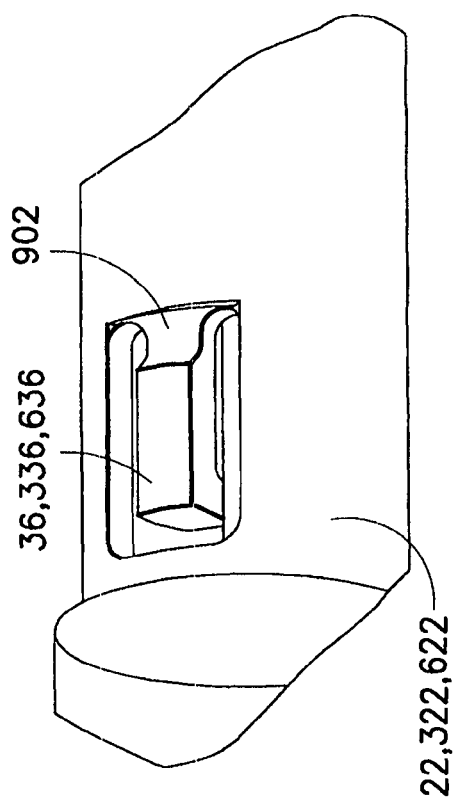
FIG. 37 is a perspective view of a shield showing an embodiment of a flexible lever arm.
Figure 38:
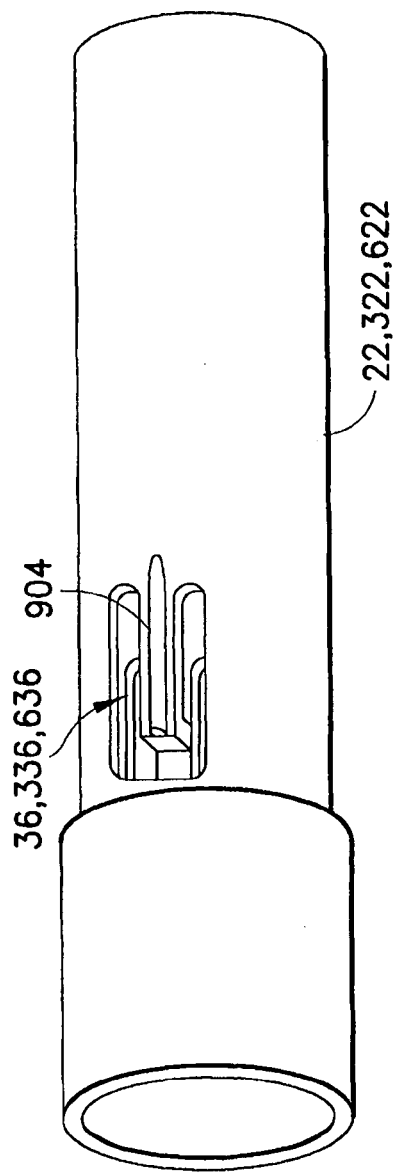
FIG. 38 is a perspective view of a shield showing another embodiment of a flexible lever arm.

In each of the above embodiments of the inventive medical devices 10, 300, 600, the lever arms 36, 336, 636 may include a recess 902 between the connection point and the free end thereof to increase the flexibility of the lever arm as shown, for example, in FIG. 37. The recess 902 may be machined. However, it is preferably formed during the manufacture of the shield 22, 622 or the front portion 360 of the syringe barrel to provide a smooth transition between the recess and the remainder of the lever arm 36, 336, 636. The smooth transition reduces the propensity of the lever arm 36, 336, 636 to fail during flexing. Alternatively, the lever arm 36, 336, 636 may be strengthened by incorporating a spine 904, as shown in FIG. 38. As shown in FIG. 38, the spine extends along the lever arm 36, 336, 636 and extends past the point of connection to increase the strength of the lever arm 36, 336, 636 in compression. The spine 904 may comprise an additional component such as a rod made of metal or other suitably strong material. The spine 904 may instead be made of the same material as the lever arm 36, 336, 636 and formed therewith as a single piece.

Figure 39:
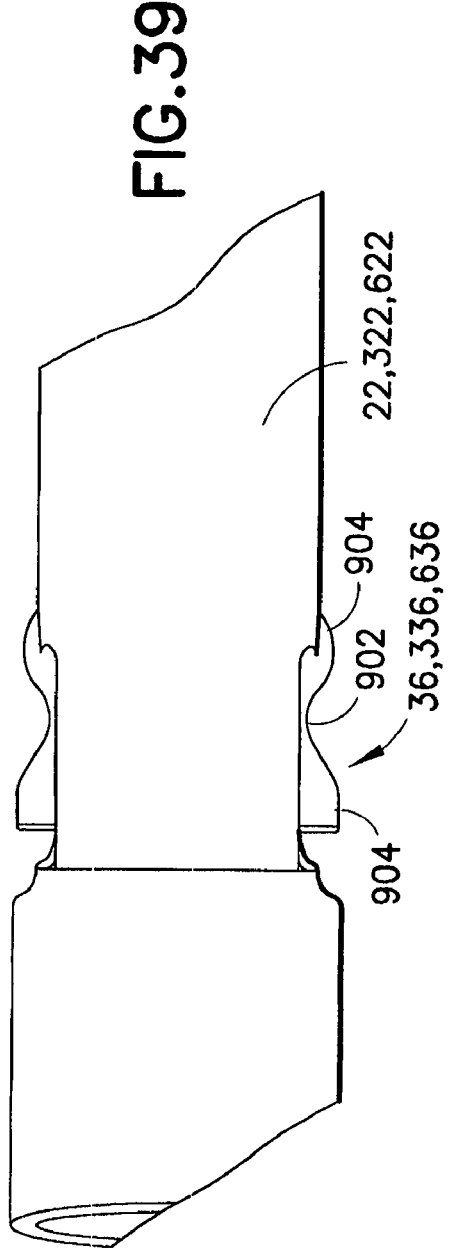
FIG. 39 is a perspective view of shield showing yet another embodiment of a flexible lever arm.

FIG. 39 shows an embodiment in which the lever arm 36, 336, 636 includes both the spine 904 and the recess 902. This embodiment provides for increased strength along the spine 904 at the point of connection to the shield and at the free end of the lever arm 36, 336, 636 while also using the recess 902 between the ends of the spine 904 providing adequate flexibility.

Figure 40:
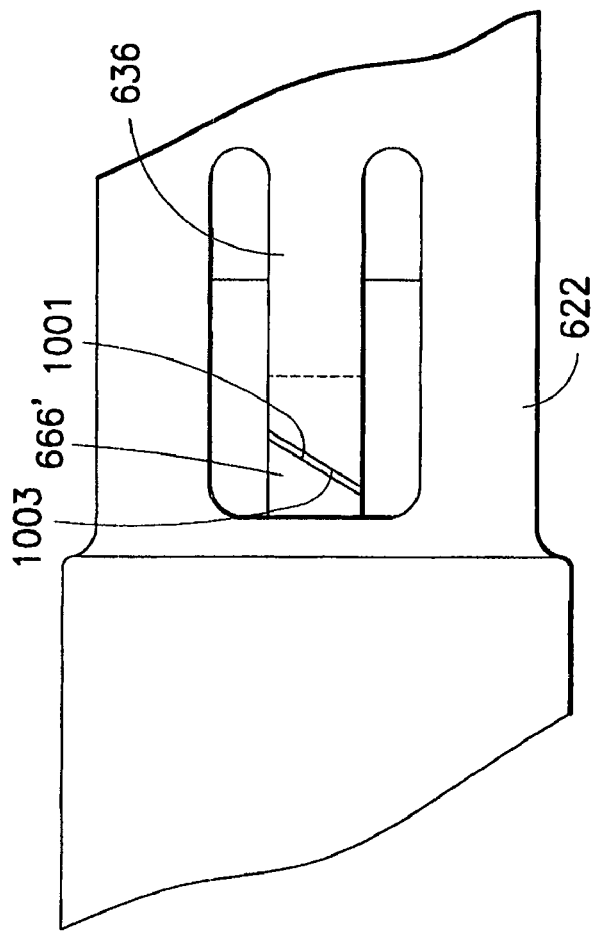
FIG. 40 is a side view of a shield showing a tangential end face of a flexible lever arm.
Figure 41:
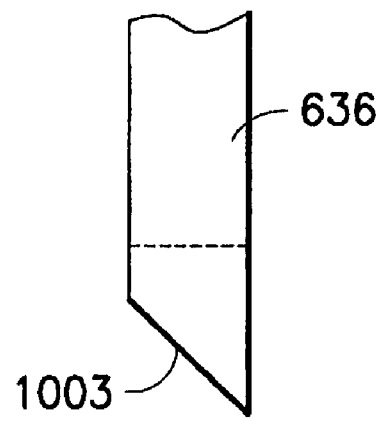
FIG. 41 is a plan view of the flexible arm of FIG. 40.
Figure 42:
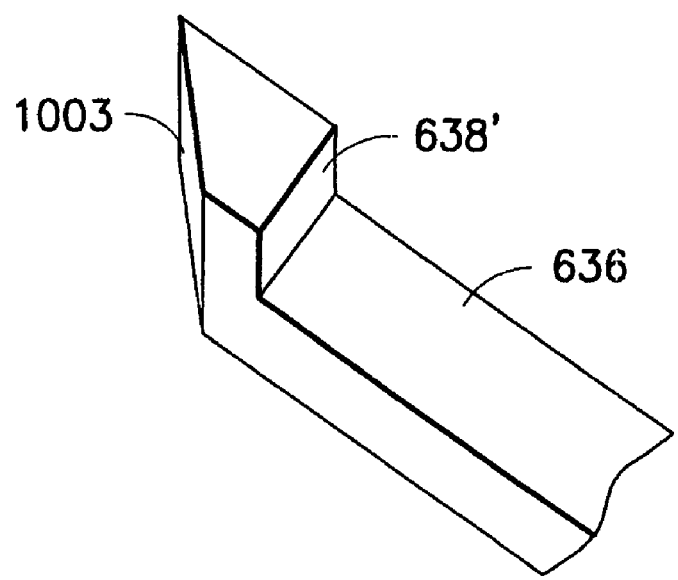
FIG. 42 is a perspective view showing the inner side of the flexible lever arm of FIG. 40.

To increase the beam buckling strength of the lever arm 636, the free end of the lever arm 636 may include a tangentially inclined surface 1003, as shown in FIGS. 40-42. The lock-out step 666' also includes a corresponding tangential inclined surface 1001 such that when the shield 622 is in the third position, the inclined surface 1001 faces the inclined surface 1003. Accordingly, the lever arm 36, 336, 636 is subject to radial and tangential bending when urged against the lock-out step 666'. This arrangement forces the lever arm 636 to bend radially and tangentially when exposed to a force which tries to push the shield 622 out of the third position, thereby preventing buckling of the lever arm 636, i.e., preventing bulging out at the center of the lever arm 636.

FIGS. 43-45 shows a reinforcement collar 906 which is connected around the shield 622. The reinforcement collar 906 is arranged proximate the connected end of the lever arm 36, 336 636 which allows flexibility and prevents the lever arm from buckling. That is, the reinforcement collar 906 prevents the center of flexible lever arm 36, 336, 636 from bulging outward. As shown in FIG. 43, the lever arm may include a recessed portion 690 on which a holding portion 910 of the reinforcement collar 906 is received. The reinforcement collar 906 may further include tabs 908 for laterally reinforcing the lever arm 636. The reinforcement collar 906 is shown as a thin strip made of a bendable material such as, for example, metal. Alternatively, the collar 906 may comprise a machined or formed metal or plastic product. Instead of tabs 908 and holding portions 910 being formed by bends in the thin strip material, the tabs and holding portions may comprise a formed ring having projection corresponding to the tabs 908 and holding portion 910.

Figure 46:
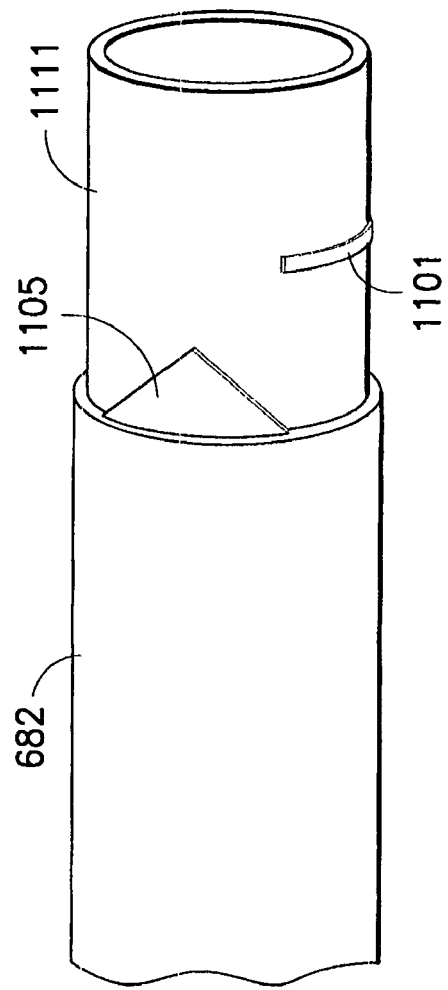
FIG. 46 is a perspective view of the cover sleeve of FIG. 16 show details of the section for receiving a needle cover.
Figure 47:
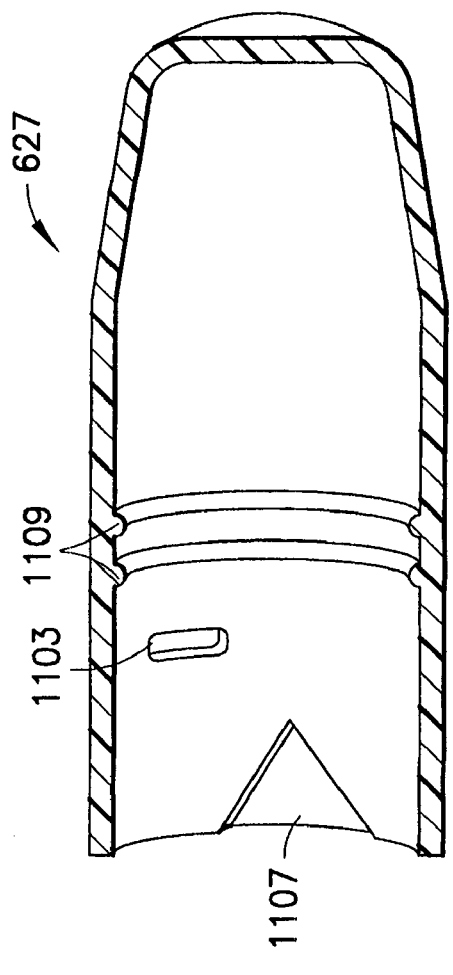
FIG. 47 is a cross-sectional view of a needle cover for the cover of FIG. 46.

FIGS. 46 and 47 show the attachment of needle cover 627 of FIG. 16 to the cover sleeve 682. As shown in FIG. 46, the cover sleeve may comprise a reduced diameter section 1111 for receiving the needle cover 627. The reduced diameter section 1111 includes an interfering projection 1105 which corresponds to a recess 1107 in the needle cover. The engagement of the interfering projection 1105 and recess 1107 causes axial movement of the needle cover 627 with regard to the cover sleeve 682 as the needle cover 627 is twisted. In addition, or alternatively, the reduced diameter section 1111 further comprises a projection 1101 corresponding to a recess 1103 in the needle cover 627 which increases the force required to move the needle cover 627 off of the cover sleeve 682 to better secure the needle cover 627 to the cover sleeve 682 during storage. The shape of the recess 1103 may be oblong to ease removal of the projection 1101 from the recess 1103 in response to torque or twisting of the needle cover 627. Finally, the needle cover 627 may also additionally or alternatively include one or more seal rings 1109 for making a sealing engagement with the reduced diameter section of the cover sleeve 682. The projections 1101, 1105 may alternatively be arranged on the needle cover 627, with the recesses 1103 and 1107 being arranged on the reduced diameter section 1111. Likewise, the seal rings 1109 may be arranged on the reduced diameter section instead of on the needle cover 627.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A medical syringe for delivering a medicament to a patient, comprising:
   a syringe assembly comprising a barrel having a forward end and a rear end and defining a reservoir within which a medicament may be contained, and a needle cannula having a forward tip and being coupled to said forward end of said barrel and in fluid communication with said reservoir;
   a hub provided on said forward end of said barrel, said hub having a rear end and a front end;
   a shield movably mounted on said hub at a first position;
   an urging member for urging said shield in a forward direction relative to said barrel; and
   a cover sleeve having a rear end connected to one of said hub and said barrel, and a front end, said cover sleeve radially surrounding at least a portion of said hub, said shield being movable from said first position to a second position against the urgency of said urging member when said needle cannula is inserted into a patient for delivery of the medicament and said shield being moveable from said second position to a third position by the influence of said urging member upon removal of said needle cannula from said patient, wherein said shield is locked in said third position and said forward tip of said needle cannula is covered by said shield when said shield is in said third position,
   wherein one of said hub and said shield defines a track arrangement having an entry track and a lock-out track, said entry track and said lock-out track being joined at an intersection, and the other of said hub and said shield includes a pin arranged on a flexible lever arm, said flexible lever arm having a base end connected to the other of said hub and said shield and a free end, said pin being arranged proximate said free end of said flexible lever arm and guidable in said track arrangement during movement of the shield between said first, second, and third positions.

2. The medical syringe of claim 1, wherein said cover sleeve and said hub are each independently connected to said barrel.

3. The medical syringe of claim 1, wherein said urging member is a coil spring arranged in the annular space between said hub and said cover sleeve.

4. The medical syringe of claim 1, wherein said cover sleeve includes a retainer arranged proximate said front end of said cover sleeve, said retainer comprising a radially inward projection interacting with a structure on said shield for blocking forward movement of said shield when said shield is in said third position.

5. The medical syringe of claim 4, wherein said retainer comprises a projection having circumferential sides and said shield comprises at least one axially extending projection arranged and dimensioned for interacting with one of said circumferential sides of said retainer to prevent said shield from rotating relative to said cover sleeve when said shield is in said third position.

6. The medical syringe of claim 4, wherein one of said shield and said cover sleeve comprises a projection and the other of said shield and said cover sleeve comprises a corresponding structure which is arranged and dimensioned for interacting with said projection for preventing said shield from rotating relative to said cover sleeve when said shield is in said third position.

7. The medical syringe of claim 1, wherein one of said shield and said cover sleeve comprises a projection and the other of said shield and said cover sleeve comprises a corresponding structure which is arranged and dimensioned for interacting with said projection for preventing said shield from rotating relative to said cover sleeve when said shield is in said third position.

8. The medical syringe of claim 1, wherein said cover sleeve comprises a first radially inward projection arranged between said front and rear ends of said cover sleeve, said shield comprising a resilient portion interacting with said projection for blocking rearward movement of said shield from said third position.

9. The medical syringe of claim 8, wherein said resilient portion comprises a flexible leg arranged on a rear portion of said shield.

10. The medical syringe of claim 9, wherein said flexible leg comprises a radial outward projection interacting with said first radially inward projection on said cover sleeve, said first radially inward projection on said cover sleeve comprising an annular ring.

11. The medical syringe of claim 10, wherein said cover sleeve includes a retainer arranged proximate said front end of said cover sleeve, said retainer comprising a second radially inward projection interacting with a structure on said shield for blocking forward movement of said shield when said shield is in said third position.

12. The medical syringe of claim 1, wherein said hub comprises a cylindrical extension, said cylindrical extension further comprising a needle guide arranged proximate said front end and defining a guide hole through which said needle cannula extends for radially supporting said needle cannula.

13. The medical syringe of claim 12, wherein said needle guide comprises a radially inward extending guide portion formed integrally as one piece with said cylindrical extension and defining said guide hole such that a diameter of said guide hole corresponds to a diameter of said needle cannula.

14. The medical syringe of claim 13, wherein said needle guide further comprises an inner cylinder connected to said guide portion and extending axially toward said rear end of said hub, said inner cylinder having an inner diameter corresponding to said diameter of said needle cannula.

15. The medical syringe of claim 12, wherein said needle guide comprises a plurality of elements extending radially inward at said front end of said cylindrical section for radially supporting said needle cannula.

16. The medical syringe of claim 12, wherein said needle guide comprises a guide element having catches arranged and dimensioned for forming one of a snap-fit and friction-fit connection in said guide hole, said needle guide further comprising a grip portion arranged and dimensioned for providing radial support to said needle cannula when said needle guide is connected in said guide hole.

17. The medical syringe of claim 1, wherein said hub defines said track arrangement, and said shield includes said pin.

18. The medical syringe of claim 17, wherein said lever arm comprises one of a recess between said base end and said free end defining a narrow portion of said flexible lever arm for reducing a force required to flex the flexible lever arm, and a spine along an axial length of said flexible lever arm to increase a strength of said flexible lever arm.

19. The medical syringe of claim 17, wherein said shield further comprises lateral projections facing opposing circumferential sides of said flexible lever arm such that said flexible lever arm abuts one of said lateral projections in response to torque on said shield to prevent rotation of said shield relative to said hub.

20. The medical syringe of claim 17, wherein said lock-out track includes a lock-out step blocking movement of said pin when said shield is in said third position, said free end of said flexible lever arm including a tangentially inclined surface facing said lock-out step when said shield is in said third position.

21. The medical syringe of claim 1, further comprising a reinforcement collar arranged on said shield for providing radial support for preventing the flexible lever arm from buckling radially outward.

22. The medical syringe of claim 21, wherein said reinforcement collar further comprises tangential supports for said flexible lever arm.

23. The medical syringe of claim 1, further comprising a needle cover, wherein said cover sleeve comprises a cylindrical portion for receiving said needle cover.

24. The medical syringe of claim 23, wherein one of said needle cover and said cylindrical portion comprises a projection and the other of said needle cover and said cylindrical portion comprises a recess corresponding to said projection for engaging said projection when said needle cover is received on said cover sleeve.

25. The medical syringe of claim 24, wherein said projection and recess are arranged and dimensioned for one of securing said needle cover on said cover sleeve and causing axial movement of said needle cover relative to said cover sleeve in response to twisting of said needle cover.

26. The medical syringe of claim 25, wherein one of said needle cover and said reduced diameter section comprise sealing rings for creating a seal between said needle cover and said reduced diameter section.

27. The medical syringe of claim 1, wherein said barrel, said hub, said cover sleeve, and said shield are made of plastic.

28. The medical syringe of claim 27, wherein said barrel and said hub are unitarily formed.

29. The medical syringe of claim 1, wherein said barrel and said hub are made of different materials.

30. A shield assembly for connection to a syringe barrel for preventing inadvertent needle sticks after use of the syringe, the shield assembly comprising a hub provided on a forward end of the syringe barrel, said hub having a rear end and a front end, a shield movably mounted on said hub at a first position, and an urging member for urging said shield in a forward direction relative to said barrel, and a cover sleeve having a rear end connected to one of said hub and the syringe barrel and a front end, said cover sleeve radially surrounding at least a portion of said hub, said shield being movable from said first position to a second position against the influence of said urging member when said needle cannula is inserted into a patient for delivery of the medicament and said shield being moveable from said second position to a third position by the urgency of said urging member upon removal of said needle cannula from said patient, wherein said shield is locked in said third position and said forward tip of said needle cannula is covered by said shield when said shield is in said third position, wherein one of said hub and said shield defines a track arrangement having an entry track and a lock-out track, said entry track and said lock-out track being joined at an intersection, and the other of said hub and said shield includes a pin arranged on a flexible lever arm, said flexible lever arm having a base end connected to the other of said hub and said shield and a free end, said pin being arranged proximate said free end of said flexible lever arm and guidable in said track arrangement during movement of the shield between said first, second, and third positions.

31. The shield assembly of claim 30, wherein said urging member is arranged in the annular space between said hub and said cover sleeve.

32. The shield assembly of claim 30, wherein said cover sleeve includes a retainer arranged proximate said front end of said cover sleeve, said retainer comprising a radially inward projection interacting with a structure on said shield for blocking forward movement of said shield when said shield is in said third position.

33. The shield assembly of claim 30, wherein one of said shield and said cover sleeve comprises a projection and the other of said shield and said cover sleeve comprises a corresponding structure which is arranged and dimensioned for interacting with said projection for preventing said shield from rotating relative to said cover sleeve when said shield is in said third position.

34. The shield assembly of claim 30, wherein said cover sleeve comprises a first radially inward projection arranged between said front and rear ends of said cover sleeve, said shield comprising a resilient leg interacting with said projection for blocking rearward movement of said shield from said third position.

35. The shield assembly of claim 30, wherein said hub comprises a cylindrical extension, said cylindrical extension further comprising a needle guide arranged proximate said front end and defining a guide hole through which said needle cannula extends for radially supporting said needle cannula.

36. The shield assembly of claim 30, wherein said hub defines said track arrangement, and said shield includes said pin.

37. The shield assembly of claim 36, wherein said lever arm comprises at least one of a recess between said base end and said free end defining a narrow portion of said flexible lever arm for reducing a force required to flex the flexible lever arm, and a spine along an axial length of said flexible lever arm to increase a strength of said flexible lever arm.

38. The shield assembly of claim 36, wherein said shield further comprises lateral projections facing opposing circumferential sides of said flexible lever arm such that said flexible lever arm abuts one of said lateral projections in response to torque on said shield to prevent rotation of said shield relative to said hub.

39. The shield assembly of claim 36, wherein said lock-out track includes a lock-out step blocking movement of said pin when said shield is in said third position, said free end of said flexible lever arm including a tangentially inclined surface facing said lock-out step when said shield is in said third position.

40. The shield assembly of claim 36, further comprising a reinforcement collar arranged on said shield for providing radial support for preventing the flexible lever arm from buckling radially outward.

41. The shield assembly of claim 30, wherein said barrel, said hub, said cover sleeve, and said shield are made of plastic.

42. The shield assembly of claim 40, wherein said barrel and said hub are unitarily formed.

43. The shield assembly of claim 30, wherein said barrel and said hub are made of different materials.

* * * * *